(12) United States Patent
Weiss et al.

(10) Patent No.: US 8,288,152 B2
(45) Date of Patent: **\*Oct. 16, 2012**

(54) SEMICONDUCTOR NANOCRYSTAL PROBES FOR BIOLOGICAL APPLICATIONS AND PROCESS FOR MAKING AND USING SUCH PROBES

(75) Inventors: Shimon Weiss, Pinole, CA (US); Marcel Bruchez, Newark, CA (US); Paul Alivisatos, Oakland, CA (US)

(73) Assignee: The Regents of the University of California, Oakland, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 12/406,651

(22) Filed: Mar. 18, 2009

(65) Prior Publication Data

US 2009/0191567 A1 Jul. 30, 2009

Related U.S. Application Data

(63) Continuation of application No. 11/566,998, filed on Dec. 5, 2006, which is a continuation of application No. 10/155,918, filed on May 24, 2002, now abandoned, which is a continuation of application No. 09/781,621, filed on Feb. 12, 2001, now Pat. No. 6,727,065, which is a continuation of application No. 09/259,982, filed on Mar. 1, 1999, now Pat. No. 6,207,392, which is a continuation-in-part of application No. 08/978,450, filed on Nov. 25, 1997, now Pat. No. 5,990,479.

(51) Int. Cl.
*C12M 1/00* (2006.01)
*C12Q 1/68* (2006.01)

(52) U.S. Cl. .......................................... 435/283.1; 435/6

(58) Field of Classification Search .................... None
See application file for complete search history.

(56) References Cited

U.S. PATENT DOCUMENTS

| | | |
|---|---|---|
| 3,954,666 A | 5/1976 | Marquisee et al. |
| 3,996,345 A | 12/1976 | Ullman et al. |
| 4,238,195 A | 12/1980 | Boguslaski et al. |
| 4,250,205 A | 2/1981 | Constant et al. |
| 4,594,264 A | 6/1986 | Jensen |
| 4,637,988 A | 1/1987 | Hinshaw et al. |
| 4,738,932 A | 4/1988 | Yabusaki |
| 4,777,128 A | 10/1988 | Lippa |
| 4,798,701 A | 1/1989 | David |
| 4,802,951 A | 2/1989 | Clark et al. |
| 4,814,668 A | 3/1989 | Tohda et al. |
| 5,084,128 A | 1/1992 | Baker |
| 5,101,827 A | 4/1992 | Goldenberg |
| 5,147,841 A | 9/1992 | Wilcoxon |
| 5,200,668 A | 4/1993 | Ohashi |
| 5,212,426 A | 5/1993 | Kane |
| 5,219,577 A | 6/1993 | Kossovsky et al. |
| 5,260,957 A | 11/1993 | Hakimi et al. |
| 5,262,357 A | 11/1993 | Alivisatos et al. |
| 5,293,050 A | 3/1994 | Chapple-Sokol et al. |
| 5,304,786 A | 4/1994 | Pavlidis et al. |
| 5,308,804 A | 5/1994 | Lee |
| 5,319,209 A | 6/1994 | Miyakawa et al. |
| 5,354,707 A | 10/1994 | Chapple-Sokol et al. |
| 5,395,791 A | 3/1995 | Cheng et al. |
| 5,422,489 A | 6/1995 | Bhargava |
| 5,427,767 A | 6/1995 | Kresse et al. |
| 5,429,824 A | 7/1995 | June |
| 5,434,878 A | 7/1995 | Lawandy |
| 5,442,254 A | 8/1995 | Jaskie |
| 5,448,582 A | 9/1995 | Lawandy |
| 5,455,489 A | 10/1995 | Bhargava |
| 5,460,831 A | 10/1995 | Kossovsky et al. |
| 5,474,591 A | 12/1995 | Wells et al. |
| 5,492,080 A | 2/1996 | Ohkawa et al. |
| 5,496,536 A | 3/1996 | Wolf |
| 5,499,260 A | 3/1996 | Takahashi et al. |
| 5,505,928 A | 4/1996 | Alivisatos et al. |
| 5,515,393 A | 5/1996 | Okuyama et al. |
| 5,525,377 A | 6/1996 | Gallagher et al. |

(Continued)

FOREIGN PATENT DOCUMENTS

CA 2029942 5/1991

(Continued)

OTHER PUBLICATIONS

U.S. Patent No. 6,322,901 (Reexamination Control No. 90/010,736)—Office Action dated Dec. 24, 2009 (NOTE: an incorrect patent number is shown on the Office Action as 6332901. The correct number should be 6322901). U.S. Patent No. 6,861,155 (Reexamination Control No. 95/001,268)—Request for Reexamination and accompanying documents and Office Action dated Feb. 4, 2010.
U.S. Patent No. 7,125,605 (Reexamination Control No. To Be Assigned)—Request for Reexamination and accompanying documents, filed Nov. 19, 2009.
Bawendi et al., "Luminescence properties of CdSe quantum crystallites: Resonance between interior and surface localized states" J. Chem. Phys., 96(12)946-954 (Jan. 15, 1992).
Alivisatos, "Semiconductor Clusters, Nanocrystals, and Quantum Dots," Science, 271:933-937 (Feb. 16, 1996).
Alivisatos, "Perspectives on the Physical Chemistry of Semiconductor Nanocrystals" J. Phys. Chem., 100:13226-13239 (1996).
Alivisatos, et al., "Organization of 'Nanocrystal Molecules' Using DNA" Nature, 382:609-611 (Aug. 15, 1996).

(Continued)

*Primary Examiner* — Eric S Dejong
(74) *Attorney, Agent, or Firm* — Knobbe, Martens, Olson & Bear, LLP

(57) ABSTRACT

A semiconductor nanocrystal compound and probe are described. The compound is capable of linking to one or more affinity molecules. The compound comprises (1) one or more semiconductor nanocrystals capable of, in response to exposure to a first energy, providing a second energy, and (2) one or more linking agents, having a first portion linked to the one or more semiconductor nanocrystals and a second portion capable of linking to one or more affinity molecules. One or more semiconductor nanocrystal compounds are linked to one or more affinity molecules to form a semiconductor nanocrystal probe capable of bonding with one or more detectable substances in a material being analyzed, and capable of, in response to exposure to a first energy, providing a second energy. Also described are processes for respectively: making the semiconductor nanocrystal compound; making the semiconductor nanocrystal probe; and treating materials with the probe.

39 Claims, 4 Drawing Sheets

U.S. PATENT DOCUMENTS

| | | |
|---|---|---|
| 5,537,000 A | 7/1996 | Alivisatos et al. |
| 5,541,948 A | 7/1996 | Krupke et al. |
| 5,565,324 A | 10/1996 | Still et al. |
| 5,585,640 A | 12/1996 | Huston et al. |
| 5,613,140 A | 3/1997 | Taira |
| 5,625,456 A | 4/1997 | Lawandy |
| 5,674,698 A | 10/1997 | Zarling et al. |
| 5,677,545 A | 10/1997 | Shi et al. |
| 5,711,803 A | 1/1998 | Pehnt et al. |
| 5,721,099 A | 2/1998 | Still et al. |
| 5,736,330 A | 4/1998 | Fulton |
| 5,747,180 A | 5/1998 | Miller et al. |
| 5,751,018 A | 5/1998 | Alivisatos et al. |
| 5,770,299 A | 6/1998 | Dannehauer et al. |
| 5,786,139 A | 7/1998 | Burke et al. |
| 5,789,162 A | 8/1998 | Dower et al. |
| 5,846,517 A | 12/1998 | Unger |
| 5,856,814 A | 1/1999 | Yagyu |
| 5,882,779 A | 3/1999 | Lawandy |
| 5,906,670 A | 5/1999 | Dobson et al. |
| 5,910,554 A | 6/1999 | Kempe et al. |
| 5,922,537 A | 7/1999 | Ewart et al. |
| 5,932,309 A | 8/1999 | Smith et al. |
| 5,939,021 A | 8/1999 | Hansen et al. |
| 5,952,665 A | 9/1999 | Bhargava |
| 5,985,173 A | 11/1999 | Gray et al. |
| 5,985,353 A | 11/1999 | Lawton et al. |
| 5,990,479 A | 11/1999 | Weiss et al. |
| 6,005,707 A | 12/1999 | Berggren et al. |
| 6,023,540 A | 2/2000 | Walt et al. |
| 6,054,495 A | 4/2000 | Markowitz et al. |
| 6,103,868 A | 8/2000 | Heath et al. |
| 6,106,609 A | 8/2000 | Yang et al. |
| 6,114,038 A | 9/2000 | Castro et al. |
| 6,139,585 A | 10/2000 | Li |
| 6,157,047 A | 12/2000 | Fujita et al. |
| 6,159,445 A | 12/2000 | Klaveness et al. |
| 6,159,742 A | 12/2000 | Lieber et al. |
| 6,165,440 A | 12/2000 | Esenaliev |
| 6,167,297 A | 12/2000 | Benaron |
| 6,179,912 B1 | 1/2001 | Barbera-Guillem et al. |
| 6,207,229 B1 | 3/2001 | Bawendi et al. |
| 6,207,392 B1 | 3/2001 | Weiss et al. |
| 6,224,739 B1 | 5/2001 | Reetz et al. |
| 6,225,198 B1 | 5/2001 | Alivisatos et al. |
| 6,251,303 B1 | 6/2001 | Bawendi et al. |
| 6,252,254 B1 | 6/2001 | Soules et al. |
| 6,262,129 B1 | 7/2001 | Murray et al. |
| 6,274,323 B1 | 8/2001 | Bruchez et al. |
| 6,294,401 B1 | 9/2001 | Jacobsen et al. |
| 6,306,610 B1 | 10/2001 | Bawendi et al. |
| 6,306,736 B1 | 10/2001 | Alivisatos et al. |
| 6,309,701 B1 | 10/2001 | Barbera-Guillam |
| 6,312,906 B1 | 11/2001 | Cass et al. |
| 6,319,426 B1 | 11/2001 | Bawendi et al. |
| 6,322,901 B1 | 11/2001 | Bawendi et al. |
| 6,326,144 B1 | 12/2001 | Bawendi et al. |
| 6,337,117 B1 | 1/2002 | Maenosono et al. |
| 6,355,432 B1 | 3/2002 | Fodor et al. |
| 6,361,944 B1 | 3/2002 | Mirkin et al. |
| 6,379,635 B2 | 4/2002 | O'Brien et al. |
| 6,410,255 B1 | 6/2002 | Pollok et al. |
| 6,417,340 B1 | 7/2002 | Mirkin et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,444,192 B1 | 9/2002 | Mattrey |
| 6,447,698 B1 | 9/2002 | Ihara et al. |
| 6,500,622 B2 | 12/2002 | Bruchez, Jr. et al. |
| 6,501,091 B1 | 12/2002 | Bawendi et al. |
| 6,506,564 B1 | 1/2003 | Mirkin et al. |
| 6,530,944 B2 | 3/2003 | West et al. |
| 6,548,168 B1 | 4/2003 | Mulvaney et al. |
| 6,548,171 B1 | 4/2003 | Barbera-Guillem et al. |
| 6,576,291 B2 | 6/2003 | Bawendi et al. |
| 6,582,921 B2 | 6/2003 | Mirkin et al. |
| 6,602,671 B1 | 8/2003 | Bawendi et al. |
| 6,607,829 B1 | 8/2003 | Bawendi et al. |
| 6,610,491 B2 | 8/2003 | Mirkin et al. |
| 6,617,583 B1 | 9/2003 | Bawendi et al. |
| 6,633,370 B2 | 10/2003 | Lawandy |
| 6,636,755 B2 | 10/2003 | Toida |
| 6,645,721 B2 | 11/2003 | Mirkin et al. |
| 6,673,548 B2 | 1/2004 | Mirkin et al. |
| 6,677,122 B2 | 1/2004 | Mirkin et al. |
| 6,682,895 B2 | 1/2004 | Mirkin et al. |
| 6,696,299 B1 | 2/2004 | Empedocies et al. |
| 6,699,723 B1 | 3/2004 | Weiss et al. |
| 6,709,825 B2 | 3/2004 | Mirkin et al. |
| 6,720,411 B2 | 4/2004 | Mirkin et al. |
| 6,727,065 B2 | 4/2004 | Weiss et al. |
| 6,730,269 B2 | 5/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,774,361 B2 | 8/2004 | Bawendi et al. |
| 6,777,186 B2 | 8/2004 | Mirkin et al. |
| 6,797,412 B1 | 9/2004 | Jain et al. |
| 6,803,719 B1 | 10/2004 | Miller et al. |
| 6,804,549 B2 | 10/2004 | Hayashi |
| 6,812,334 B1 | 11/2004 | Mirkin et al. |
| 6,815,064 B2 | 11/2004 | Treadway et al. |
| 6,818,753 B2 | 11/2004 | Mirkin et al. |
| 6,819,692 B2 | 11/2004 | Klimov et al. |
| 6,821,337 B2 | 11/2004 | Bawendi et al. |
| 6,828,432 B2 | 12/2004 | Mirkin et al. |
| 6,846,565 B2 | 1/2005 | Korggel et al. |
| 6,855,551 B2 | 2/2005 | Bawendi et al. |
| 6,858,158 B2 | 2/2005 | Chittibabu et al. |
| 6,861,155 B2 | 3/2005 | Bawendi et al. |
| 6,861,221 B2 | 3/2005 | Mirkin et al. |
| 6,864,626 B1 | 3/2005 | Weiss et al. |
| 6,872,249 B2 | 3/2005 | Peng et al. |
| 6,878,814 B2 | 4/2005 | Mirkin et al. |
| 6,890,777 B2 | 5/2005 | Bawendi et al. |
| 6,902,895 B2 | 6/2005 | Mirkin et al. |
| 6,903,207 B2 | 6/2005 | Mirkin et al. |
| 6,914,265 B2 | 7/2005 | Bawendi et al. |
| 6,921,496 B2 | 7/2005 | Anderson et al. |
| 6,927,069 B2 | 8/2005 | Weiss et al. |
| 6,962,786 B2 | 11/2005 | Mirkin et al. |
| 6,969,761 B2 | 11/2005 | Mirkin et al. |
| 6,984,491 B2 | 1/2006 | Mirkin et al. |
| 6,986,989 B2 | 1/2006 | Mirkin et al. |
| 7,049,148 B2 | 5/2006 | Bawendi et al. |
| 7,060,243 B2 | 6/2006 | Bawendi et al. |
| 7,098,320 B1 | 8/2006 | Mirkin et al. |
| 7,101,718 B2 | 9/2006 | Weiss et al. |
| 7,125,605 B2 | 10/2006 | Bawendi et al. |
| 7,138,098 B2 | 11/2006 | Bawendi et al. |
| 7,160,613 B2 | 1/2007 | Bawendi et al. |
| 7,169,556 B2 | 1/2007 | Park et al. |
| 7,181,266 B2 | 2/2007 | Frangioni et al. |
| 7,189,417 B2 | 3/2007 | Chen et al. |
| 7,208,587 B2 | 4/2007 | Mirkin et al. |
| 7,235,361 B2 | 6/2007 | Bawendi et al. |
| 7,250,499 B2 | 7/2007 | Mirkin et al. |
| 7,259,252 B2 | 8/2007 | Mirkin et al. |
| 7,314,764 B2 | 1/2008 | Weiss et al. |
| 6,947,979 B1 | 3/2011 | Celanese |
| 2001/0023078 A1 | 9/2001 | Bawendi et al. |
| 2001/0040232 A1 | 11/2001 | Bawendi et al. |
| 2002/0066401 A1 | 6/2002 | Peng et al. |
| 2002/0071952 A1 | 6/2002 | Bawendi et al. |
| 2002/0072234 A1 | 6/2002 | Weiss et al. |
| 2002/0146714 A1 | 10/2002 | Lieber et al. |
| 2003/0017264 A1 | 1/2003 | Treadway et al. |
| 2003/0042850 A1 | 3/2003 | Bertram et al. |
| 2003/0099968 A1 | 5/2003 | Weiss et al. |
| 2003/0100130 A1 | 5/2003 | Weiss et al. |
| 2003/0113709 A1 | 6/2003 | Alivisatos et al. |
| 2003/0209105 A1 | 11/2003 | Bawendi et al. |
| 2004/0036085 A1 | 2/2004 | Sato et al. |
| 2004/0104973 A1 | 6/2004 | Nabiev et al. |
| 2004/0265622 A1 | 12/2004 | Sadasivan et al. |
| 2005/0020922 A1 | 1/2005 | Frangioni et al. |

| | | | |
|---|---|---|---|
| 2005/0020923 | A1 | 1/2005 | Frangioni et al. |
| 2005/0038498 | A1 | 2/2005 | Dubrow et al. |
| 2005/0113697 | A1 | 5/2005 | Ottoboni et al. |
| 2005/0118631 | A1 | 6/2005 | Bawendi et al. |
| 2005/0175540 | A1 | 8/2005 | Oraevsky et al. |
| 2005/0220714 | A1 | 10/2005 | Kauzlarich et al. |

FOREIGN PATENT DOCUMENTS

| | | |
|---|---|---|
| EP | 0 990 903 | 4/2000 |
| EP | 1 271 154 A2 | 1/2003 |
| JP | 64-500196 | 1/1989 |
| JP | 03-258866 | 11/1991 |
| JP | 09-510828 | 10/1997 |
| JP | 10-328571 | 12/1998 |
| WO | 88/00060 | 1/1988 |
| WO | WO 91/06894 | 5/1991 |
| WO | WO 93/10564 | 5/1993 |
| WO | WO 93/26019 | 12/1993 |
| WO | WO 94/07142 | 3/1994 |
| WO | WO 94/11103 | 5/1994 |
| WO | 95/26042 | 9/1995 |
| WO | WO 95/29473 | 11/1995 |
| WO | WO 96/10282 | 4/1996 |
| WO | WO 97/10175 | 3/1997 |
| WO | WO 98/04740 | 2/1998 |
| WO | WO 98/19963 | 5/1998 |
| WO | WO 98/33080 | 7/1998 |
| WO | WO 98/36376 | 8/1998 |
| WO | WO 98/46372 | 10/1998 |
| WO | WO 98/55844 | 12/1998 |
| WO | WO 99/19515 | 4/1999 |
| WO | WO 99/25299 | 5/1999 |
| WO | WO 99/26299 | 5/1999 |
| WO | WO 99/50916 | 10/1999 |
| WO | WO 00/17103 | 3/2000 |
| WO | WO 00/17642 | 3/2000 |
| WO | WO 00/17655 | 3/2000 |
| WO | WO 00/17656 | 3/2000 |
| WO | WO 00/27365 | 5/2000 |
| WO | WO 00/27436 | 5/2000 |
| WO | WO 00/28088 | 5/2000 |
| WO | WO 00/28089 | 5/2000 |
| WO | WO 01/07689 | 2/2001 |
| WO | WO 2005/004253 | 2/2005 |
| WO | WO 2005/017951 | 2/2005 |

OTHER PUBLICATIONS

Beverloo et al., "Inorganic Phosphors as New Luminescent Labels for Immunocytochemistry and Time-Resolved Microscopy," Cytometry, 11:784-792 (1990).

Beverloo et al., "Preparation and Microscopic Visualization of Multicolor Luminescent Immunophosphors," Chapter 4 of Beverloo, H.B., "Inorganic Crystals as Luminescent Labels: Their Applications in Immunocytochemistry and Time-Resolved Microscopy" Ph.D. dissertation, University of Leiden (The Netherlands), May 13, 1992, pp. 553-573.

Bigham et al., "Deactivation of Q-CdS Photoluminescence through Polynucleotide Surface Binding" The Journal of Physical Chemistry, 96(26):10581-10583 (Dec. 24, 1992).

Bigham, "Influence of Properties Polynucleotide Stabilizers on Selected Properties of Quantum-Confined Cadmium Sulfide Semiconductor Clusters," Thesis submitted to Graduate Faculty of AddRan College of Arts and Sciences Texas Christian University (Feb. 1996).

Bigham et al., "The influence of adenine content on the properties of Q-Cds clusters stabilized by polynucleotides" Colloids and Surfaces A: Physiochemical and Engineering Aspects, 95:211-219 (Feb. 20, 1995).

Bruchez, "Luminescent Semiconductor Nanocrystals: Intermittent Behavior and Use as Fluorescent Biological Probes" Ph.D. dissertation, University of California, Dec. 17, 1998.

Bruchez et al., "Semiconductor Nanocrystals as Fluorescent Biological Labels" Science, 281:2013-2016 (Sep. 25, 1998).

Bruchez et al., "Semiconductor Nancrystals as Fluorescent Probes for Biology" Cytometry Supp. 9:26 (1998).

Chan et al., "Quantum Dot Bioconjugates for Ultrasensitive Nonisotopic Detection" Science, 281:2016-2018 (Sep. 25, 1998).

Chandler et al., "Spectroscopic Analysis of Semiconductor Colloids" Journal of Chemical Education, 70:A7-A10 (Jan. 1993).

Coffer et al., "Nucleotides as Structural Templates for the Self-Assembly of Quantum-Confined CdS Crystallites" R.R. Material Research Society Symposium Proceedings, 206:527-531 (1991).

Coffer et al., "Dictation of the shape of mesoscale semiconductor nanoparticle assemblies by plasmid DNA" Applied Physics Letter, 69(25):3851-3853 (Dec. 16, 1996).

Coffer et al., "Characterization of Quantum-Confined CdS Nanocrystallites Stabilized by Deoxyribunucleic Acid (DNA)" Nanotechnol. 3:69-76 (1992).

Colvin et al., "Semiconductor Nanocrystals Covalently Bound to Metal Surfaces with Self-Assembled Monolayers" J. Am. Chem. Soc., 114:5221-5230 (1992).

Cook, "Scintillation Proximity Assay: A Versatile High-Throughput Screening Technology," Drug Discovery Today, 1:287-294 (Jul. 1996).

Correa-Duarte et al., "Stabilization of CdS Semiconductor Nanoparticles Against Photodegradation by a Silica Coating Procedure" Chem. Phys. Lett., 286:497-501 (Apr. 17, 1998).

Dabbousi et al., "(CdSe)ZnS Core-Shell Quantum Dots: Synthesis and Characterization of a Size Series of Highly Luminescent Nanocrystalities" Journal of Physical Chemistry B, 101:9463-9475 (1997).

Ashwood et al., "Synthesis and Antihypertensive Activity of 4-(Substituted-carbonylamino)-2H-1-benzopyrans" J. Med. Chem., 33:2667-2672 (1990).

Dameron et al., "Glutathione-coated Cadmium-Sulfide Crystallites in Candida glabrata" The Journal of Biological Chemistry, 264(29):17355-17360 (Oct. 15, 1989).

Dameron et al., "Biosynthesis of cadmium sulphide quantum semiconductor crystallites" Nature, 338:596-597 (Apr. 13, 1989).

Dameron et al., "Characterization of Peptide-Coated Cadmium-Sulfide Crystallites" Inorg. Chem., 29:1343-1348 (1990).

Danek et al., "Synthesis of Luminescent Thin-Film Quantum Dot Composites Using CdSe Quantum Dots Passivated with an Overlayer of ZnSe" Chem. Mater., 8:173-180 (1996).

Haughland, "Handbook of Fluorescent Probes and Research Chemicals," Molecular Probes (sixth edition) (Nov. 1996).

Hermanson, "Bioconjugate Techniques" Academic Press (New York) (Jan. 15, 1996).

Hines et al., "Synthesis and Characterization of Strongly Luminescing ZnS-Capped CdSe Nanocrystals" J. Phys. Chem., 100:468-471, (1996).

Jacoby, "Quantum Dots Meet Biomolecules," C&E News, 76:copied from the Internet as pp. 1-3 (Sep. 28, 1998).

Kagan, et al., "Electronic Energy Transfer in CdSe Quantum Dot Solids" Phys. Rev. Lett, 76:1517-1520 (Feb. 26, 1996).

Kortan et al., "Nucleation and Growth of CdSe on ZnS Quantum Crystallite Seeds, and Vice Versa, in Inverse Micelle Media" J. Am. Chem. Soc, 112:1327-1332 (1990).

Lacoste et al., "Super Resolution Molecular Ruler Using Single Quantum Dots" Biophysical Journal, 78:402A, XP-000933548 Abstract (Jan. 2000).

Lawless et al., "Bifunctional Capping of CdS Nanoparticles and Bridging to TiO2" J. Phys. Chem., 99:10329-10335 (1995).

Lawton et al., "Biomolecular Self-Assembly of Quantum-Dot Composites" Materials Research Symposium Proceedings vol. 330 (Biomolecular Materials by Design), pp. 283-288 (1994).

Leff,, "Color-coding Quantum Dots Debut with Promising Careers in Clinical Diagnostics Field," Bioworld Today, copied from the internet as pp. 1-2 (Sep. 25, 1998).

Liz-Marzan et al., "Synthesis of Nanosized Gold-Silica Core-Shell Particles" Lanqmuir, 12:4329-4335 (1996).

Mahtab et al., "Preferential Adsorption of a 'Kinked' DNA to a Neutral Curved Surface: Comparisons to and Implications for Non-specific DNA-Protein Interactions," J. Am. Chem. Soc., 118:7028-7032 (1996).

Mahtab et al., "Protein-Sized Quantum Dot Luminescence Can Distinguish Between 'Straight,' 'Bent,' and 'Kinked' Oligonucleotides," J. Am. Chem. Soc., 117:9099-9100 (1995).

Mirkin et al., "A DNA-based method for rationally assembling nanoparticles into macroscopic materials" Nature, 382:607-609 (Aug. 15, 1996).

Murphy et al., "Quantum Dots as Inorganic DNA-Binding Proteins," Mat. Res. Soc., Symp. Proc., 452:597-600 (1997).

Nirmal et al., "Fluorescence Intermittency in singlecadmium selenide nanocrystals" Nature, 353:802-804 (Oct. 31, 1996).

Peng et al., "Epitaxial Growth of Highly Luminescent CdSe/CdS Core/Shell Nanocrystals with Photostability and Electronic Acessibility" Journal of American Chemical Society, 119(30):7019-7029, (1997).

Peng et al., "Synthesis and Isolation of a Homodimer of Cadmium Selenide Nanocrystals," Angewandte Chemie-International Edition in English, 36:145-147 (1997).

Rajh et al., "Synthesis and Characterization of Surface-Modified Colloidal CdTe Quantum Dots" J. Phys. Chem., 97:11999-12003 (1993).

Rogach et al., "Synthesis and Characterization of Thiol-Stabilized CdTe Nanocrystals" Bren. Bunsengesm Physical Chemistry (vol. 100, No. 11, pp. 1772-1778 (Jul. 1996).

Service, "Semiconductor Beacons Light Up Cell Structures," Science, 281:1930-1931 (Sep. 25, 1998).

Shrock et al., "Multicolor Spectral Karyotyping of Human Chromosomes," Science, 273:494-497 (Jul. 26, 19196), (1996).

Tobin et al., "Photoemission investigation of compound semiconductor monodisperse clusters" J. Vac. Sci. Technol. A 9(3):852-853 (May 1, 1991).

Weller et al., "Nanocrystals of II-VI Semiconductor Materials" Materials Research Symposium Proceedings vol. 358 Microcrystalline and Nanocrystalline Semiconductors), pp. 213-218 (1995).

Weller et al., "Optical Properties of Quantized Semiconductor Particles" Philosophical Transactions of the Royal Society: A. (vol. 354(1708), pp. 757-766 (Mar. 15, 1996).

Zhang et al., "Novel Flow Cytometry Compensation Standards: Internally Stained Fluorescent Microspheres with Matched Emission Spectra and Long-Term Stability" Cytometry, 33:244-248 (1998).

Aktsipetrov, O.A., et al. "Generation of reflected second harmonic at semiconductor quantum dots," *JETP Letters*, vol. 55, No. 8, 435-439 (1992).

Alivisatos, et al., "Electronic states of semiconductor clusters: Homogeneous and inhomogeneous broadening of the optical spectrum," *J. Chem. Phys.* 89:4001-4011, 1988.

Alivisatos, et al., "Electron-vibration coupling in semiconductor clusters studied by resonance Raman spectroscopy," *J. Chem. Phys.* 90:3463-3468, 1989.

Alivisatos, et al., "Resonance Raman scattering and optical absorption studies of CdSe microelusters at high pressure," *J. Chem. Phys.* 89:5979-5982, 1988.

Bain, et al., "Strong Molecular Alignment in Anisotropic Fluid Media," *Chem. Phys. Lett*, 260:441-446, 1996.

Baltrameyunas, R., et al., "Fast switching of the transmission of light by glasses activated with CdS microcrystals," *Sov. Phys. Semicond.*, vol. 25 No. 2, 164-166 (1991).

Baltramiejunas, R., et al. "Rapid Processes of Darkening and Bleaching in CdS Doped Glasses," *Superlattices and Microstructures* vol. 10, No. 3, 307-310 (1990).

Bawendi, et al., "Electronic Structure and Photoexcited-Carrier Dynamics in Nanometer-Size CdSe Clusters," *Phys. Rev. Lett.* 65:1623-1626, 1990.

Bawendl et al., "X-ray Structural Characterization of Larger CdSe Semiconductor Clusters," *J. Chem. Phys.* 91:7282-7290, 1989.

Berry. et al., "Melting of Clusters and Melting," *Phys. Rep. A* 30:919-931, 1984.

Bhargava, et al., "Quantum Confined Atoms of Doped ZnO Nanocrystals,"*phys. slat. sot* (*b*) 229:897-901, 2002.

Bimberg et al., "Luminescence properties of semiconductor quantum dots", 1997, J. Luminescence (vol. 72-74. pp. 34-37).

Bopp, et al., "Single-Molecule Spectroscopy With 27 fs Pulses: Time-Resolved Experiments and Direct Imaging of Orientational Distributions,"*Appl. Phys. Lett.* 73:7-9, 1998.

Braun, et al., "Electroluminescence and Electrical Transport in Poly(3-octylthiophene) Diodes," *J. Appl. Phys.* 72:564-568, 1992.

Brown, et at, "Polytp-pitenylenevinylene) Light-Emitting Diodes: Enhanced Electroluminescent Efficiency Through Charge Carrier Confinement," *Appl. Phys. Lett.* 61:2793-2795, 1992.

Brus, "Zero-Dimensional 'Excitons' in Semiconductor Clusters," *IEEE J. Quantum Electronics* QE_22:1909-1914, 1987.

Brus, "A Simple Model for the Ionization Potential, Electron Affinity, and Aqueous Redox Potentials of Small Semiconductor Crystallites," *J. Chem. Phys.* 79:5566-5571, 1983.

Brus, "Electron-Electron and Electron-Hole Interactions in Small Semiconductor Crystallites: The Size Dependence of the Lowest Excited Electronic State"*J. Chem. Phys.* 80:4403-4409, 1984.

Buffat and Borel., "Size Effect on the Melting Temperature of Gold Particles," *Phys. Rev. A* 13:2287-2298, 1976.

Bunge, et al., "Growth and Morphology of Cadmium Chalcogonides; The Synthesis of Nanorods, Tetrapods, and Spheres from CdO and $Cd(O_2 CCH_2)_2$." *J. Mater. Chem.* 13:1705-1709, 2003.

Callomon, et at, "Rotational Analysis of the 2600 Angstrom Absorption System of Benzene," *Phil. Trans. R. Soc. Land.* A 259:499-512, 1966.

Chamarro, M., et al., "Enhancement of Exciton Exchange Interaction by Quantum Confinement in CdSe Nanocrystals," *Jpn. J. Appl. Phys*, vol. 34, 12-14 (1994).

Chamarro, M., et al., "Size-dependent Electron-Hole Exchange Interaction in CdSe Quantum Dots, *II Nuovo Cimento*," vol. 17, Nos. 11-12, (1995) 1407-1412.

Chamarro, et al,"Enhancement of Electron-Hole Exchange Interaction in CdSe Nanocrystals; A Quantum Confinement Effect." *Phys. Rev. B* 53:1336-1342, 1996.

Chamarro, et at,"Photoluminescenca Polarization of Semiconductor Nanocrystals,"*J. Lumin.* 70:222-237, 1996.

Chamarro et al., "Optical properties of Mn-doped CdS nanocrystals", 1996, J. of Crystal Growth (vol. 159, pp. 853-856).

Chepic, D.I., et al., "Auger ionization of semiconductor quantum drops in a glass matrix," *Journal of Luminescence* 47 (1990) 113-127 North-Holland.

Czarnik, "Encoding methods for combinatorial chemistry" *Curr Opin Chem Biol.*, 1(1):60-66, 1997.

Danek et al., "Preparation of II-VI quantum dot composites by electrospray organometallic chemical vapor deposition." Journal of Crystal Growth, vol. 145 (1994), p. 714-720.

Database Crossfire Online!; Beilstein Institut zur Forderung der Chemischen Wissenschaft; Beilstein Registry Nos. 2097823 and 1860016; XP002152687—Abstract.

Dickson, et al., "Simultaneous Imaging of Individual Molecules Aligned Both Parallel and Perpendicular to the Optic Axis," *Phys. Rev. Lett.* 81:5322-5325, 1998.

Dneproviskii, V.S., et al., "Time-Resolved Luminescence of CdSe Microcrystals," *Solid State Communications*, vol. 74, No. 7, pp. 555-557, 1990.

Edamatsu, et al., "Subpicosecond Dynamics of Confined Excitons and Optical Nonlinearities of CuCI Quantum Dots," *J. Lumia.* 66-67:406-409, 1996.

Efros, A.L., et al., "Resonance Raman Spectroscopy of Electron-Hole Pairs—Polar Phonon Coupling in Semiconductor Quantum Microcrystals," *Solid State Communications*, vol. 78, No. 10, pp. 853-856, 1991.

Efros, "Luminescence Polarization of CdSe Microcrystals,"*Phys. Rev. B* 46:7448-7458, 1992.

Egner et al., "Tagging in combinatorial chemistry: the use of coloured and fluorescent bads" *Chem. Commun.*, 735-736, Apr. 21, 1997.

Ekimov, A. I., et al., "Absorportion and intensity-dependent photoluminescence measurements on CdSe quantum dots: assignment of the first electronic transitions," *Journal of the Optical Society of America*, vol. 10, Nos. 1-12, 100-107 (1992).

Ekimov, A.I., "Optical Properties of Oxide Glasses Doped by Semiconductor Nanocrystals," *Radiation Effects and Defects in Solids*, 1995, vol. 134, pp. 11-22.

Ekimov, A.I., "Optical Properties of Semiconductor Quantum Dots in Glass Matrix," *Physica Scripta.* vol. T39, 217-222 (1991).

Ekimov, A.I., et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Ekimov, A.I., et al., "Spectra and Decay Kinetics of Radiative Recombination in CdS Microcrystals," *Journal of Luminescence* 46 (1990) 83-95 North-Holland.
Ekimov, A.I., et al., "Donor-like Exciton in Zero-Dimension Semiconductor Structures," *Solid State Communications*, vol. 69, No. 5, pp. 565-568, 1989.
Ekimov, A.I., et al., "Influence of high hydrostatic pressures on the exciton spectrum of CdS microcrystals in glass," *Sov. Phys. Semicond.* 23(9), Sep. 1989, pp. 965-966.
Ekimov, A.I., et al., "Nonlinear Optics of Semiconductor-Doped Glasses," *Phys. Stat. Sol.* (b) 150, (1988) pp. 627-633.
Ekimov, A.I., et al., "Optics of Zero Dimensional Semiconductor Systems, *Acta Physica Polonica A*," vol. 79 (1991), No. 1. pp. 5-14.
Ekimov, A.I., et al., "Photoluminescence of quasizero-dimensional semiconductor structures," *Sov. Phys. Solid State* 31(8), Aug. 1989, pp. 1385-1393.
Ekimov, A.I., et al., "Quantization of the energy spectrum of holes in the adiabatic potential of the electron," JETP Lett., vol. 43, No. 6, Mar. 25, 1986, pp. 376-379.
Ekimov, A.I., et al., "Quantum Size Effect in Semiconductor Microcrystals," *Solid State Communications*, vol. 56, No. 11, pp. 921-924, 1985.
Ekimov, A.I., et al., "Quantum size effect in the optical spectra of semiconductor microcrystals," *Sov. Phys. Semicond.* 16(7), Jul. 1982, pp. 775-778.
Ekimov, A.I., et al., "Quantum-Size Stark Effect in Semiconductor Microcrystals," *Journal of Luminescence* 46 (1990) 97-100 North-Holland.
Ekimov, A.I., et al., "Size quantization of the electron energy spectrum in a microscopic semiconductor crystal," *JETP Lett.*, vol. 40, No. 8, Oct. 25, 1984, pp. 1136-1139.
Ekimov, "Growth and Optical Properties of Semiconductor Nanocrystals in a Glass Matrix," *J. Lumin.* 70:1-20, 1996.
Ekimov, el al., "Growth of CdSe Nanocrystals in ton-Implanted $SiO_2$ Films,"*J. Cryst. Growth* 151:38-45, 1995.
Franceschetti, et al., "Many-Body Pseudopotential Theory of Excitons in InP and CdSe Quantum Dots," *Phys. Rev. B* 60:1819-1829, 1999.
Gelbart et al., "The 'New' science of 'complex fluids'", 1996, J. Phys. Chem. (vol. 100, pp. 13169-13189).
Grabovskis, V.Y., et al., "Photoionization of semiconducting microcrystals in glass," *Sov. Phys. Solid State* 31(1), Jan. 1989, pp. 149-151.
Green, et at "Recent Advances in the Preparation of Semiconductors as Isolated Nanometric Particles: New Routes to Quantum Dab," *Chem. Commun.* 1999:2235-2241, 1999.
Guha et al., "Hybrid organic-inorganic semiconductor-based light-emitting diodes" *J. Appl. Phys.*, 82(8):4126-4128, Oct. 15, 1997.
Gurevich, S.A., et al. "Preparation and investigation of $SiO_2$ films activated by CdS semiconductor nanocrystals," *Soviet Physics Semiconductors*, vol. 26, 57-59 (1992).
Guttler, et at, "Single Molecule Polarization Spectroscopy: Pentacene in p-Terphertyl," *Chem. Phys.* 211:421-430, 1996.
Ha, et al., "Single Molecule Dynamics Studied by Polarization Modulation," *Phys Rev. Lett.* 77:3979-3982, 1996.
Haase, et at, "Photochemistry and Radiation Chemistry of Colloidal Semiconductors. 23. Electron Storage on ZnO Particles and Size Quantization," *J. Phys. Chem.* 92:482-487, 1988.
Hahn and Whetten, "Rigid-Fluid Transition in Specific-Size Argon Clusters," *Phys. Rev. Lett.* 61:1190-1193, 1988.
Harrison et al., "Wet chemical synthesis of highly luminescent HgTe/CdS core/shell nanocrystals", 2000, Adv. Mater. (vol. 12, No. 2, 123).
Hermann, et al, "Immunogold Labeling in Scanning Electron Microscopy," *Histochem Cell Biol.* 106:31-39. 1996.
Honeycutt and Andersen, "Molecular Dynamics Study of Melting and Freezing of Small Lennard-Jones Chisters,"*J. Phys. Chem.* 91:4950-4963, 1987.
Huang et al., "Assembly and applications of the inorganic nanocrystals in polymer networks", 1998, Thin Solid Films (vol. 327-329, pp. 536-540).
Huynh, et al., "CdSe Nanocryalal Rods/Poly (3-hexylthiophene) Composite Photovoltaic Devices," *Adv. Mater.* 11:923-927, 1999.

Itoh, et al, "Pohlman and Exciton-Phonon Complexes in CuCl Nanocrystals," *Phys. Rev. Lett.* 74:1645-1648, 1995.
Itoh, T. et al., "Interface effects on the properties of confined excitons in CuCl microcrystals," *Journal of Luminescence* 60 & 61 (1994) 396-399.
Itoh, T., et al., "Subpicosecond dynamics of confined excitons in CuCl nanocrystals," *Materials Science and Engineering* A217/218 (1996) 167-170.
Jarvis, Jr. et al "Solution Synthesis and Photoluminenscence Studies of Small Crystallites of Cadmium Telluride," *Mat. Res. Soc. Symp. Proc.*, 272:229-235 (1992).
Jursenas, S., et al., "Surface Recombination of Nonequilibrium Electron-Hole Plasma in Laser-Modified Semiconductor-Doped Glasses," *Solid State Communications*, vol. 87, No. 6, 577-580 (1993).
Kabay, et al.."Remaval of Metal Pollution (Cd(11) and Cr (111)) from Phocphotle Add Solutions by Chelating Resins Containing Phosphonic or Diphosphonic Groups," *Ind. Eng. Chem. Res.* 37:2541-2547, 1991.
Klein, et al., "Scanned Probe Investigations of Chemically Derived Nanostructures," *Nanotechnology* 7:397-400,1996.
Kovalev, et al., "Optically Induced Polarization Anisottophy in Porous Si," *Phys. Rev. Lett.* 77:2089-2092, 1996.
Kuno, et al., "Magnetic Circular Dichroism Study of CdSe Quantum Dots," *J. Chem. Phys.* 108:4242-4247, 1998.
Kuno et al., "The band edge luminescence of surface modified CdSe nanocrystallites," *Mater. Res. Soc. Symp. Proc.* 1996, 452, 347-352.
Lee, et al, "Full Color Emission from II-VI Semiconductor Quantum Dot-Polymer Composites," *Adv. Mater.* 12:1102-1105, 2000.
Lee, et al., "Adsorption of Ordered Zirconium Phosphonate Multilayer Films on Silicon and Gold Surfaces," *J. Phys. Chem* 92:2597-2601, 1988.
Leppert, et al., "Structural and Optical Characteristics of ZnSe Nanocrystals Synthesized in the Presence of a Polymer Capping Agent," *Mater. Sci. Eng. B Solid State* 52:89-92, 1998.
Leung, et al., "Exicton Fine Structure in CdSe Nanoclusters," *Phys. Rev. B* 57:12291-12301, 1998.
Lieber, "One-Dimensional Nanostructures: Chemistry, Physics & Applications", *Solid State Commun.* 167:607-616, 1998.
Litigation Documents. Western District of Wisconsin. Docket No. 09-cv-00258. *Nanosys, Inc.* v. *Nanoco Technologies Ltd.* and *Sigma-Aldrich Co.*
Liu and Risbud, "Quantum-Dot Size-Distribution Analysis and Precipitation Stages in Semiconductor Doped Glasses," *J. Appl. Phys.* 68:28-32, 1990.
Loher et al., "Epitaxy films of the 3D semiconductor CdS on the 2D layered substrate MX2 prepared by Van der Walls epitaxy," Journal of Crystal Growth, 1995, 146, 408-412.
Lublinskaya, et al., "CdS Nanocrystal Growth in Thin Silica Films: Evolution of Size Distribution Function," *J. Cryst. Growth* 184-185:360-364, 1998.
Ludolph, et al., "Novel Single Molecule Piscurser Routes for the Direct Synthesis of Highly Monodispersed Quantum Dots of Cadmimm or Zinc or Solonide," *Chem. Commun.* 1998:1849-1850, 1998.
Malik, et al., "Semiconductor Nanoparticles: Their Properties, Synthesis and Potential for Application," *S. Afr. J. Sei.* 96:55-60, 2000.
Masumoto et al., "Preparation of monodisperse CdS nanocrystals by size selective photocorrosion." *J. Phys. Chem.* 100(32): 13782 (1996).
Mattoussi, et al., "Bioconjugation of Highly Luminescent Colloidal CdSe-ZaS Quantum Dots with on Engineered Two-Domain Recombinant Protein,"*phys. stat. sol.* (b) 224:277-283, 2001.
Mews et al., "Structural and spectroscopic investigations of CdS/HgS/CdS quantum-dot quantum wells," *Phys. Rev. B* 1996, 53, R13242-R13245.
Mikulec, F.V. et al., Synthesis and characterization of highly luminescent (CdSe)ZnS quantum dots: Advances in microcrystalline and nanocrystalline semiconductors, Symposium 1996, Boston, MA, Mater. Res. Soc. 1997, Pittsburgh, PA, USA, Dec. 2-6, 1996, pp. 359-364.

Miller, et at.. "Electroabsorption of Highly Confined System. Theory of the Quantum-Confined Franz-Keldysh Effect in Semiconductor Quantum Wires and Dots."*Appl. Phys. Lett.* 52:2154-2156, 1988.

Miller, et al., "Relation Between Electroabsorption in Bulk Semiconductors and in Quantum Wells: The Quantum-Confined Franz-Keldysh Effect," *Phys. Rev. B* 33:6976-6982, 198-6.

Moffitt et al., "Spherical assemblies of semiconductor nanoparticles in water-soluble block copolymer aggregates", 1998, Chem. Mater. (vol. 10, pp. 1021-1028).

Murray, et al., "Colloidal Synthesis of Nanocrystals and Nanocrystal Superlanices,"*IBM J. Res. Dev.* 45:47-56, 2001.

Murray, "Preparation and properties nanocrystals and nanocrystal superlattices: Building with artificial atoms." 2004.

Murray, C. B., "Synthesis and characterization of II-IV quantum dots and their assembly into 3D quantum dot superlattices." 1995. Thesis.

Nicolaou et al., "Radiofrequency Encoded Combinatorial Chemistry" *Ingew. Chem. Int. Ed. Engl.*, 34(20):2289-2291, 1995.

Nirmal, et al., "Observation of the 'Dark Exciton' in CdSe Quantum Dots," *Phys. Rev. Lett.* 75:3728-3731,1995.

Norris and Bawendi, "Measurement and Assignment of the Size-Dependent Optical Spectrum in CdSe Quantum Dots.," *Phys. Rev. B* 53:16338-16346, 1996.

Norris, et al., "Size Dependence of Exciton Fine Structure in CdSe Quantum Dots," *Phys. Rev. B* 53;16347-16354, 1996.

Ohnishi, "Electroluminescent display materials", 1989, Annu. Rev. Mater. Sci. (vol. 19, pp. 83-101).

Olshaysky et al., "Synthesis of CdS nanoparticles in solution and in a polyphosphazene matrix", 1997, Chem. Mater. (vol. 9, pp. 1367-1376).

Pileni et al., "Synthesis of Cadmium sulfide in situ in reverse micelles: influence of the preparation modes on size, polydispersity, and photochemical reactions", 1992, Chem. Mater. (vol. 4, pp. 338-345).

Rogach et al., "Layer-by-layer assembled films of HgTe nanocrystals with strong infrared emission", 2000, Chem. Mater. (vol. 12, pp. 1526-1528).

Routkevitch, et al., "Electrochemical Fabrication of CdS Nanowire Arrays in Porous Anodic Aluminum Oxide Templates," *J. Phys. Chem*, 100:14037-14047, 1996.

Saviot, et al., "Size dependence of acoustic and optical vibrational modes of CdSe nanocrystals in glasses," *Journal of Non-Crystalline Solids* 197:238-246, 1996.

Saviot, et al., "Size-Selective Resonant Raman Scattering in CdS Doped Glasses," *Phys. Rev. B* 57:341-346,1998.

Saviot, L., et al., "Effects of Resonance on Low-Frequency Raman Scattering From Semiconductor Nanocrystals," *Radiation Effects and Defects in Solids*, 1995, vol. 137, pp. 45-50.

Schlamp, et al., "Improved Efficiencies in Light Emitting Diodes Made with CdSe (CdS) Core/Shefl Type Nanocrystals and a Semiconducting Polymer,"*J. Appl. Phys.* 82:5837-5842. 1997.

Schmitt-Rink. et al., "Theory of the Linear and Nonlinear Optical Properties of Semiconductor Microcrystallites," *Phys. Rev. B* 35:8113-8125, 1987.

Service, "Materials Science: Small clusters hit the big time", 1996, Science (vol. 271, pp. 920-922).

Sheng, et al., "Melting Transition of Small Molecular Clusters," *J. Phys. C* 14:L565-L569, 1981.

Shiang, et al., "Lattice Reorganization in Electronically Excited Semiconductor Clusters," *J. Chem. Phys.* 92:3232-3233, 1990.

Shiang, et al., "Symmetry of Annealed Wurtzite CdSe Nanocrystals: Assignment to the $C_3$, Point Group." *J. Phys. Chem.* 99:17417-17422, 1995.

Sirenko, et al., "Spin-Flip and Acoustic-Phonon Raman Scattering in CdS Nanocrystals," *Phys. Rev. B* 58:2077-2087, 1998.

Smith, et al, "Measurement of Rotational Motion in Membranes Using Fluorescence Recovery After Photobleaching," *Biophys. J.* 36:73-91, 1981.

Tamulaitis, G., et al., "Dynamics of Nonlinear Optical Response of CuBr-Doped Glasses," *Superlattices and Microstructures*, vol. 3, No. 2, 199-202 (1993).

Tang, et al., "Electroluminescence of Doped Organic Thin Films," *J. Appl. Phys.* 65:3610-3616, 1989.

Tang and Vanslyke, "Organic Elecirolumineacent Diodes," *Appl. Phys. Lett* 51:913-915, 1987.

Tillman, et al., "Oxidation of a Sulfide Group in a Self-Assembled Monolayer," *Langmuir* 5:1020-1026, 1989.

Tsuji et al., "Characterization of CdS thin film in high efficient CdS/CdTe solar cells", *Journal of Crystal Growth*, vol. 214/215, 2000, pp. 1142-1147.

Valenta, et al., "Dynamics of Excitons in CuBr Nanocrystals: Spectral-Hole Burning and Transient Four-Wave-Mixing Measurements," *Phys. Rev. B* 57:1774-1783, 1998.

Vandyshev, Y.V., et al., "Nonlinear optical properties of semiconductor microcrystals," JETP Lett., vol. 46, No. 10, Nov. 25, 1987 pp. 435-439.

Volkov, A.S., et al., "Oscillations of polarization of recombination radiation of a variable gap semiconductor in a magnetic field," JETP Lett., vol. 25 No. 55, 526-528 (1977).

Wang, et al., "Synthesis and Characterization of MSe (M=Zn, Cd) Nanorods by a New Solvothennal Method," *Inorg. Chem. Commun.* 2:83-85, 1999.

Watzke et al., "Quantum size effects of in situ generated colloidal CdS particles in Dioctadecyldimethylammonium chloride surfactant vesicles", 1987, J. Phys. Chem. (vol. 91, pp. 854-861).

Wegener, "Fluorescence Recovery Spectroscopy as a Probe of Slow Rotational Motions," *Biophys. J* 46:795-803, 1984.

Winzelar, et al., "Direct Allelic Variation Scanning of the Yeast Genome," *Science* 281:1194-1197, 1998.

Yang et al., "Epitaxial growth of size-quantized cadmium sulfide crystals under arachidic acid monolayers", 1995, J. Phys. Chem. (vol. 99, pp. 5500-5504).

Zhao and Fendler, "Semiconductor Particulate Films on Solid Supports," *Chem. Mater.* 3:168-174, 1991.

Zhao and Fendler, "Size Quentitization in Semiconductor Particulate Films," *J. Phys. Chem.* 95:3716-3723,1991.

U.S. Appl. No. 60/031,809, Jul. 29, 1996, C.A. Mirkin et al.

Aggarwal et al., "Insights into US public biotech sector using patenting trends", 2006, Nature Biotechnology (vol. 24, No. 6, 643).

Akerman, et al., "Nanocrystal Targeting in vivo," Proc. Natl. acad. Sci. USA 99:12617-12621, 2002.

Allara and Nuzzo, "Spontaneously Organized Molecular Assemblies. 1. Formation, Dynamics, and Physical Propesties of n-Alkani Acids Abosorbed from Solution of an Oxidized Aluminum Surface," *Langmuir* 1:45-52, 1985.

Allara and Nuzzo, "Spontaneously Organized Molecular Assemblies. 2. Quantitative Infrared Spectroscope Destermination of Equlbrium Structures of Solution-Absorbed n-Alkanic Acids on an Oxidized Aluminum Surface," *Langmuir* 1:52-66, 1985.

Bain and Whitesides, "Formation of Monolayers by the Coadsorption of Thiols on Gold: Variation in the Length of the Alkyl Chain," *J. Am. Chem. Soc.* 111:7164-7175, 1989.

Bain, et al., "Comparison of Self-Assembled Monolayers on Gold: Coadsorption of Thiols and Disulfides," *Langmuir* 5:723-727, 1989.

Bain, et al., "Formation of Monolayer Films by the Spontaneous Assembly of Organic Thiols from Solution on Gold," *J. Am. Chem. Soc.* 111:321-335, 1989.

Bain, et al., "Formation of Monolayers by the Coadsorption of Thiols on Gold: Variation in the Head Group, Tail Group, and Solvent," *J. Am. Chem. Soc.* 111:7155-7164, 1989.

Baldwin et al., "Synthesis of a small molecule combinatorial library encoded with molecular tags," *J. Am. Chem. Soc.*, 117: 5588-5589, 1995.

Betzig and Chichester, "Single Molecules Observed by Near-Field Scanning Optical Microscopy," *Science* 262:1422-1425, 1993.

Brus, "Electronic Wave Functions in Semicondcutor Clusters: Experiment and Theory," J. Phys. Chem. 90:2555-2560, 1986.

Byrne, et al., "Design of a Monomeric Arsinogallane and Chemical Conversation to Gallium Arsenide," *Science* 241:332-334, 1988.

Chee et al., "Accessing Genetic Information with High-Density DNA Arrays" Science, 274(5287):610-614, Oct. 25, 1996.

Chikan et al., "Synthesis of highly luminescent GaSe nanoparticles", 2002, Nano Letters (vol. 2, No. 2, 141-145).

Chisey and Loiacono, "Chemical Functionality in Self-assembled Monolayers: Structural and Electrochemical Properties," *Langmuir* 6:682-691, 1990.

Chidsey, "Free Energy and Tempertature Dependence of Electron Transfer at the Metal-Electrolytc Interface," *Science* 251:919-922, 1991.

Chidsey, et al., "Coadsorption of Ferrocene-Terminated and Unsubstituted Alkanethiols on Gold: Electroactive Self-Assembled Monolayers," *J. Am. Chem. Soc.* 112:4301-4306, 1990.

Colvin et al., "Light-emitting diodes made from cadmium selenide nanocrystals and a semiconducting polymer" *Nature*, 370(6488):354-357, Aug. 4, 1994.

Cumberland et al. "Inorganic clusters as single source precursors for preparation of CdSe, ZnSe, and CdSe/AnS nanomaterials," *Chem. Mater.* 2002, 14, 1576-1584.

Dabbousi, et al., "Electroluminescence from CdSe Quantum-Dot/Polymer Composites," *Appl. Phys. Lett.* 66:1316-1318, 1995.

De Paula et al "Quantum confinement effects on the optical phonons of CdTe quantum dots," *Superlattices and Microstructures* 23:1103-1106 (1998).

de Oliveira et al "Probing of the quantum dot size distribution in CdTe-doped glasses by photoluminescence excitation spectroscopy," *Appl. Phys. Lett.* 66:439-441 (1995).

Efros, et al., "Band-Edge Exciton in Quantum Dots of Semiconductors With a Degenerate Valence Band: Dark and Bright Exciton States," *Phys. Rev. B* 54:4843-4856, 1996.

Ekimov, A.I., et al., "Quantum size effect in three-dimensional microscopic semiconductor crystals," *JETP Lett*, vol. 34, No. 6, Sep. 20, 1981, pp. 345-349.

Elghanian, et al., "Selective Colorimetric Detection of Polynucleotides Based on the Disance-Dependent Optical Properties of Gold Nanoparticles," *Science* 277:1078-1081, 1997.

Empedocles and Bawendi, "Quantum-Confined Stark Effect in Single CdSe Nanocrystalite Quantum Dots," *Science* 278:2114-2117, 1997.

Empedocles, et al., "Three-Dimensional Orientation Measurements of Symmetric Single Chromophores Using Polarization Microscopy," *Nature* 399:126-130, 1999.

Empedocles et al., "Photoluminescence spectroscopy of single CdSe nanocrystallite quantum dots," *Phys. Rev. Lett.*, 77(18): 3873 (1996).

Fodor, "Techwire" *Science*, 277(5324):393-395, Jul. 18, 1997.

Fox., et al., "Fluoresence and Rodox Activity of Probes Anchored through an Aminotrithiol to Polycrystalline Gold," *Langmuir* 14:816-820, 1998.

Gan, et al., "Enhanced Photoluminescence and Characterization of Mn-Doped ZnS Nanocrystallites Snthesized in Microemulsion," *Langmuir* 13:6427-6431, 1997.

Gao et al "Strongly Photoluminescent CdTe Nanocrystals by Proper Surface Modification," *J. Phys. Chem. B.* 102:8360-8363 (1998).

Gao, et al., "In vivo Cancer Targeting and Imaging with Semiconductor Quantum Dots," *Nat. Biotechnol.* 22:969-976, 2004.

Goldsitn et al., "Melting in Semiconductor Nanocrystals," *Science* 256:1425-1427, 1992.

Han, et al., "Quantum-Dot-Tagged Microbeads for Multiplexed Optical Coding of Biomolecules," *Nat. Biotechnol.* 19:631-635, 1991.

Han, et al., "Synthesis of Gallium Nitride Nanorods Through a Carbon Nanotube-Confined Reaction," *Science* 277:1287-1289, 1997.

Hickman, et al., "Combining Spontaneous Molecular Assembly with Microfabrication to Pattern Surfaces: Selective Binding of Isonitiles to Plutsinum Microwaves and Characterization by Electrochemistry and Surfaces Spectoscopy," *J. Am. Chem. Soc.* 11:7271-7272, 1989.

Huibers et al., "Prediction of critical micelle concentration using a quantitative structure-property relationship approach. 1. Nonionic surfactants", 1996, *Langmuir* (vol. 12, pp. 1462-1470).

Kagen, et al., "Long-Range Resonance Transfer of Electronic Excitations in Close-Packed CdSe Quantum-Dot Solids," *Phys. Rev. B* 54:8633-8643, 1996.

Kneipp, et al., "Single Molecule Detection Using Surface-Enhanced Raman Scattering (SERS)," *Phys. Rev. Lett.* 78:1667-1670, 1997.

Kuno, et al., "The Band Edge Luminescence of Surface Modified CdSe Nanocrystallites: Probing the Luminescing State," *J. Chem. Phys.* 106:9869-9882, 1997.

Kuroda et al. "Micro photoluminescence spectra of CdTe and CdMnTe self-organized quantum dots,", *Journal of Luminescence* 83-84:321-342 (1999).

Lee et al., "Surface Derivatization of Nanocrystalline CdSe Semiconductors," *Mat. Res. Soc. Symp. Proc.*, 452:323-328, Mar. 13, 1997.

Macklin, et al., "Imaging and Time-Resolved Spectoscopy of Single Molecules at an Interface," *Science* 272:255-258, 1996.

Mahtab et al., "Preferential-Absorption of a 'Kinked' DNA to a Neutral Curved Surface: Comparison to and Implications for Nonspecific DNA-Pprotein Interactions," *J. Am. Chem. Soc.*, 118(30):7028-7032, 1996.

Maoz and Sagiv, "Penetration-Controled Reactions in Organized Monolayer Assemblies. 1. Aqueous Permanganste Interaction with Monolayer and Multilayer Films of Long-Chaim Surfactants," *Langmuir* 3:1034-1044, 1987.

Mattoussi, et al., "Self-Assembly of CdSe-ZnS Quantum Dot Bioconjugates Using an Engineered Recombinant Protein," *J. Am. Chem. Soc.* 122:12142-12150, 2000.

McGall et al., "Light-directed synthesis of high-density oligonucleotide arrays using semiconductor photoresists" *Proc. Natl. Acad. Sci. USA*, 93:13555-13560, Nov. 1996.

Michael, et al., "Randomly Ordered Addressable High-Density Optical Sensor Arrays," *Anal. Chem.* 70:1242-1248, 1998.

Mićić et al., "Core-Shell Quantum Dots of Lattice-Matched ZnCdSe$_2$ Shells on InP Cores: Experiment and Theory," *J. Phys. Chem. B* 2000, 104 (51), 12149-12156.

Moran et al., "Radio Frequency Tag Encoded Combinatorial Library Method for the Discovery of Tripeptide-Substituted Cinnamic Acid Inhibitors of the Protein Tyrosine Phosphatase PTP1B" *J. Am. Chem. Soc.*, 117:10787-10788, 1995.

Müllenborn et al., "Characterization of Solution-Synthesized CdTe and HgTe," *Applied Physics*, 56:317-321, 1993.

Murray et al.; "Synthesis and Characterization of Nearly Monodisperse CdE (E=S,Se,Te) Semiconductor Nanocrystallites"; *.J. Am. Chem. Soc* 115; pp. 8709-8715 (1993).

Nuzzo and Allara, "Adsorption of Bifuncational Organic Disulfides on Gold Surfaces," *J. Am. Chem. Soc.* 105:4481-4483, 1983.

Nuzzo, et al., "Spontaneously Organized Molecular Assemblies. 3. Prparation and Properties of Solution Adsorbed Monolayers of ORganic Disulfides on Gold Surfaces," *J. Am. Chem. Soc.* 109:2358-2368, 1987.

Olshavsky, et al., "Organometallic Synthesis of GaAs Crystallites Exhibiting Quantum Confinement," *J. Am. Chem. Soc.* 112:9438-9439, 1990.

Pale-Grosdemange, et al., "Femation of Self-Assembled Monolayers by Chemisorption of Derivatives of Oligo (ethyleme glycol) of Structure HS(CH$_2$)$_3$(OCH$_2$CH$_2$)$_x$OH on Gold," *J. Am. Chem. Soc.* 113:12-20, 1991.

Pehnt et al., "Nanoparticle precursor route to low-temperature spray deposition of CdTe thin films," *Appl. Phys. Lett.*, 67(15):2176-2178, Oct. 1995.

Peng, et al., "Kinetics of II-VI and III-V Colloidal Semiconductor Nanocrystal Growth: 'Focusing' of Size Distributions," *J. Am. Chem. Soc.* 120:5343-5344, 1998.

Porter, et al., "Spontaneously Organized Molecular Assemblies. 4. Structural Characterization of n_Alkyl Thiol Monolayers on Gold by Optical Elliposmetry, Infrared Spectroscopy, and Electrochemistry," *J. Am. Chem. Soc.* 109:3559-3568, 1987.

Putvinski, et al., "Self-Assembly of Organic Multilayers with Polar Order Using Zirconium Phosphate Bonding Between Layers," *Langmuir* 6:1567-1571, 1990.

Qiu et al., "Study of the core-shell nanoparticle formed through the 'coil-to-globule' transition of poly(N-isopropylacrylamide) grafted with poly(ethylene oxide)", 1997, *Macromolecules* (vol. 30, pp. 7921-7926).

Resch et al "Photochemistry and Radiation Chemistry of Colloidal Semiconductors. 33. Chemical Changes and Fluorescence in CdTe and ZnTe," *Langmuir* 5:1015-1020 (1989).

Ridley, et al., "All-Inorganic Field Effect Transistors Fabricated by Printing," *Science* 286:746-749, 1999.

Rockenberger et al "An EXAFS Study on Thiolcapped CdTe Nanocrystals," *Ber. Bunsenges. Phys. Chem.* 102:1561-1564 (1998).

Rogach et al "Synthesis, Morphology and Optical Properties of Thiol-Stabilized CdTe Nanoclusters in Aqueous Solution," *Ber. Bunsenges. Phys. Chem.* 101:1668-1670 (1997).

Rubinstein, et al., "Ionic Recognition and Selective Response in Self-Assembling Monolayer Membranes on Electrodes," *Nature* 332:426-429, 1988.

Ruiter, et al., "Single Molecule Rotational and Translational Diffusion Observed by Near-Field Scanning Optical Microscopy," *J. Phys. Chem. A* 101:7318-7323, 1997.

Sandroff, et al., "GaAs Clusters in the Quantum Size Regime: Growth on High Surface area Silica by Molecular Beam Epitaxy," *Science* 245:391-393, 1988.

Schröck et al., "Multicolor Spectral Karyotyping of Human Chromosomes," *Science*, 273:494-497, Jul. 26, 1996.

Spanhel et al., "Photochemistry of Colloidal Semiconductors. Surface Modification and Stability of Strong Luminescing CdS Particles" *J. Am. Chem. Soc.*,109(19):5649-5655, 1987.

Steigerwald et al., "Surface Derivatization and Isolation of Semiconductor Cluster Molecules," *J. Am. Chem. Soc.*, 110:3046-3050, 1988.

Strong and Whitesides, "Structures of Self-Assembled Monolayer Films of Organosaulfur Compounds Absorbed on Gold Single Crystals: Electron Diffraction Studies," *Langmuir* 4:546-558, 1988.

Taiapin et al., "PbSe nanocrystal solids for n- and p-channel thin film field-effect transistors", 2005, Science (vol. 310, pp. 86-89).

Tillmam, et al., "Formation of Multilayers by Self-Assembly," *Langmuir* 5:101-111, 1989.

Toth et al., "Structure of BRIJ-35 nonionic surfactant in water: a reverse monte carlo study", 2006, Langmuir (vol. 22, pp. 590-597).

Ulman, et al., "Packing and Molecular Orientation of Alkamethiol Monolayers on Gold Surfaces," *Langmuir* 5:1147-1152, 1989.

Ulman and Tillman, "Self-Assembling Double Layers on Gold Surfaces: The Merging of Two Chemistries," *Langmuir* 5:1418-1420, 1989.

Wang, et al., "Synthesis and Characterization of MSe (M=Zn, Cd) Nanorods by a New Solvothermal Method," *Inorg. Chem. Commun.* 2:83-85, 1999.

Wasserman, et al., "Structure and Reactivity of Alkylsiloxane monolayers Formed by Reaction of Alkyltrichlorosilures on Silicon Substrates," *Langmuir* 5:1074-1087, 1989.

Wasserman, et al., "The Structure of Self-Assembled Monolayers of Alkylsiloxanes on Silicon: A Comparison of Results from Elipsometry and Low-Angle X-ray Reflexativity," *J. Am. Chem. Soc.* 111:5852-5861, 1989.

Whitesell et al., "Directionally Aligned Helical Peptides on Surfaces" *Science*, 261:73-76, Jul. 2, 1993.

Wu, et al., "Immunofluorescent Labeling of Cancer Marker Her2 and Other Cellular Targets with Semiconductor Quantum Dots," *Nat. Biotechnol.* 21:41-46, 2003.

Zen, et al., "Scanning Tunneling Microscopic Imaging of CdS Q Particles Prepared in Acetonitrile solution," *Langmuir* 5:1355-1358, 1989.

Jones-Bey, Hassaun "Biological Imaging" Laser Focus World, vol. 35, No. 1, Jan. 1999, pp. 1-2.

U.S. District Court, East District of Texas, Civil Docket for Case # 6:08-cv-00163-LED-JDL; *Invitrogen Corporation et al. v. Evident Technologies, Inc. et al.*; filed Apr. 29, 2008; terminated Jul. 10, 2009; Assigned to Judge Leonard Davis; referred to Magistrate Judge John D. Love; Jury Demand: Plaintiff; Cause: 15:1126 Patent Infringement; Nature of Suite: 830 Patent; Jurisdiction: Federal Question.

U.S. District Court, Southern District of California (San Diego), Civil Docket for Case #: 3:08-cv-01729-JAH-LSP; *eBioscience Corporation v. Invitrogen Corporation et al.*; filed Sep. 22, 2008; terminated Apr. 20, 2009; assigned to Judge John A. Houston; referred to Magistrate Judge Leo S. Papas; Jury Demand: Plaintiff; Cause: 35:145 Patent Infringement; Nature of Suite: 830 Patent; Jurisdiction: Federal Question.

U.S. District Court, Southern District of California (San Diego), Civil Docket for Case #: 3:310-cv-IEG-NLS; *Life Technologies Corporation et al. v. Ebioscience Inc.*; filed Oct. 12, 2010; assigned to Judge Irma E. Gonzalez; referred to Magistrate Judge Nita L. Stormes; Cause: 28:1338 Patent Infringement; Nature of Suit: 830 Patent; Jurisdiction: Federal Question.

Molecular Biology and Biotechnology: A comprehensive desk reference, p. 458 (Robert A. Meyer ed.) (1995).

Morgan et al., "Immunosensors: technology and opportunities in laboratory medicine," Clin. Chem, 42:193-209 (1996).

Wenthold et al., "Glycine immunoreactivity localized in the cochlear nucleus and superior olivary complex" Neuroscience, 22:897-912 (1987).

Grant & Hackh's Chemical Dictionary, pp. 403 and 540 (Roger Grant and Clair Grant eds., 5th ed.) (1987).

A Dictionary of Chemistry, pp. 84, 208, 306 and 528 (John Daintith ed., 3rd ed.) (1996).

Genes V, pp. 1103-1106 (Benjamin Lewin ed., Oxford University Press) (1984).

Declaration of Heather Milliken, Senior Acquisition Specialist, ProQuest LLC (Oct. 30, 2008, pp. 1-2.

Molecular Biology of the Cell, pp. 4 and 88-89 (Bruce Alberts et al. eds., Garland Publishing, Inc. 2d ed. 1989) (1983).

Dictionary of Modern Biology, p. 297 (Norah Rudin) (1997).

Complaint for Patent Infringement and Jury Trial Demanded, in the matter *Invitrogen Corporation, Quantum Dot Corporation, Molecular Probes, Inc. v. Evident Technologies Inc., and DOES* 1 through 5, Inclusive, and Regents of the University of California, in U.S. District Court for the Eastern District of Texas Tyler Division, Docket No. 6:08-cv-00163, dated Apr. 29, 2008.

Notice of Filing Patent Action, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Apr. 30, 2008.

First Amended Complaint for Patent Infringement, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Jun. 19, 2008.

Defendant's Invalidity Contentions, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit I to Defendant's Invalidity Contentions: U.S. Patent No. 6,423,551, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit II to Defendant's Invalidity Contentions: U.S. Patent No. 6,423,551, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit III to Defendant's Invalidity Contentions: U.S. Patent No. 6,699,723, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit IV to Defendant's Invalidity Contentions: U.S. Patent No. 6,699,723, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit V to Defendant's Invalidity Contentions: U.S. Patent No. 6,927,069, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.

Exhibit VI to Defendant's Invalidity Contentions: U.S. Patent No. 6,927,069, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.
Exhibit VII to Defendant's Invalidity Contentions: Declaration of Heather Milliken, dated Oct. 30, 2008, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Nov. 7, 2008.
Plaintiffs' Reply to Counterclaim, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Jan. 28, 2009.
Consent Judgment and Permanent Injunction, in the matter *Invitrogen Corporation, Quantum Dot Corporation, Molecular Probes, Inc., and Regents of the University of California v. Evident Technologies Inc., and DOES* 1 through 5, Inclusive, in U.S. District Court for the Eastern District of Texas Tyler Division, Docket No. 6:08-cv-00163, dated Jun. 29, 2010.
Complaint for Declaratory Judgment of Non-Infringement and Invalidity of U.S. Patent No. 6,423,551, U.S. Patent No. 6,699,723, and U.S. Patent No. 6,927,069, Jury Trial Demanded, in the matter *Ebioscience Corporation, v. Invitrogen Corporation, Quantum Dot Corporation, and Molecular Probes, Inc.*, in U.S. District Court Southern District of California, Docket No. 3:08-cv-01729, dated Sep. 22, 2008.
Notice of Related Case, in the matter *Ebioscience Corporation, v. Invitrogen Corporation, Quantum Dot Corporation, and Molecular Probes, Inc.*, in U.S. District Court Southern District of California, Docket No. 3:08-cv-01729, dated Sep. 24, 2008.
Order Granting Defendants' Motion to Dismiss and Dismissing the Complaint in its Entirety, in the matter *Ebioscience Corporation, v. Invitrogen Corporation, Quantum Dot Corporation, and Molecular Probes, Inc.*, in U.S. District Court Southern District of California, Docket No. 3:08-cv-01729, dated Apr. 20, 2009.
Clerk's Judgment, in the matter *Ebioscience Corporation, v. Invitrogen Corporation, Quantum Dot Corporation, and Molecular Probes, Inc.*, in U.S. District Court Southern District of California, Docket No. 3:08-cv-01729, dated Apr. 20, 2009.
Complaint and Jury Demand, in the matter *Life Technologies Corporation, Molecular Probes, Inc. and the Regents of the University of California v. Ebioscience Inc.*, in U.S. District Court Southern District of California, Docket No. 3:10-cv-02127, dated Oct. 12, 2010.
Notice of Related Cases, in the matter *Life Technologies Corporation, Molecular Probes, Inc. and the Regents of the University of California v. Ebioscience Inc.*, in U.S. District Court Southern District of California, Docket No. 3:10-cv-02127, dated Oct. 14, 2010.
Defendant Ebioscience Inc's Answer to Plaintiffs' Complaint and Counterclaims, in the matter *Life Technologies Corporation, Molecular Probes, Inc. and the Regents of the University of California v. Ebioscience Inc.*, in U.S. District Court Southern District of California, Docket No. 3:10-cv-02127, dated Jan. 6, 2011.
Defendant Ebioscience, Inc.'s Preliminary Invalidity Contentions, in the U.S. District Court for the Southern District of California, Docket No: 10-CV-2127-IEG, dated May 16, 2011.
Request for Ex Parte ReExamination of U.S. Patent No. 6,927,069 Exhibit A to Ebioscience's Preliminary Invalidity Contentions, in the matter *Life Technologies Corporation, Molecular Probes, Inc. and the Regents of the University of California v. Ebioscience Inc.*, in U.S. District Court Southern District of California, Docket No. 3:10-cv-02127, dated May 13, 2011.
Request for Ex Parte ReExamination of U.S. Patent No. 6,423,551 Exhibit B to Ebioscience's Preliminary Invalidity Contentions, in the matter *Life Technologies Corporation, Molecular Probes, Inc. and the Regents of the University of California v. Ebioscience Inc.*, in U.S. District Court Southern District of California, Docket No. 3:10-cv-02127, dated May 13, 2011.
Request for Ex Parte ReExamination of U.S. Patent No. 6,699,723 Exhibit C to Ebioscience's Preliminary Invalidity Contentions, in the matter *Life Technologies Corporation, Molecular Probes, Inc. and the Regents of the University of California v. Ebioscience Inc.*, in U.S. District Court Southern District of California, Docket No. 3:10-cv-02127, dated May 13, 2011.
Plaintiffs' Reply to Ebioscience, Inc's Counterclaims, in the matter *Life Technologies Corporation, Molecular Probes, Inc. and the Regents of the University of California v. Ebioscience Inc.*, in U.S. District Court Southern District of California, Docket No. 3:10-cv-02127, dated Jan. 27, 2011.
Plaintiffs' First Amended Complaint and Jury Demand, in the matter *Life Technologies Corporation, Molecular Probes, Inc. and the Regents of the University of California v. Ebioscience Inc.*, in U.S. District Court Southern District of California, Docket No. 3:10-cv-02127, dated Apr. 12, 2011.
Defendant Ebioscience, Inc's Answer to Plaintiffs' First Amended Complaint and Counterclaims, in the matter *Life Technologies Corporation, Molecular Probes, Inc. and the Regents of the University of California v. Ebioscience Inc.*, in U.S. District Court Southern District of California, Docket No. 3:10-cv02127, dated Apr. 29, 2011.
Gurevich, S.A., et al., "Growth of CdS nanocrystals in silicate glasses and in thin Si02 films in the initial states of the phase separation of a solid solution," Semiconductors, 28 (5), May 1994, 486-493.
Plunkett et al., "Combinatorial Chemistry and New Drugs," Sci Am., 276(4):68-73, Apr. 1997.
Answer to Amended Complaint, Counterclaim against Invitrogen Corporation, Quantum Dot Corporation, Molecular Probes, Inc., Regents of the University of California by Evident Technologies, Inc. (Attachments #1 Exhibit 1, #2 Exhibit 2, #3 Exhibit 3) (Wilcox, Melvin), dated Jan. 7, 2009.
Claim Construction Chart filed by Evident Technologies, Inc., Invitrogen Corporation, Quantum Dot Corporation, Molecular Probes, Inc., Regents of the University of California, DOES 1 through 5, inclusive. (Attachments: #1 Exhibit A, #2 Exhibit B) (Johnson, Kristine), dated Jun. 24, 2009.
Corrected Request for Reexamination of U.S. Patent No. 6,699,723 (Control No. 90/009,909), dated Jun. 9 ,2011.
Corrected Request for Reexamination of U.S. Patent No. 6,699,069 (Control No. 90/009,908), dated Jun. 9, 2011.
Order Granting Joint Motion to Stay; Denying as Moot Defendant's Motion to Stay, in the matter *Life Technologies Corporation, Molecular Probes, Inc., and the Regents of the University of California vs. Ebioscience, Inc.*, in U.S. District Court for Southern District of California, Docket No. 10cv2127-IEG (NLS), dated Jul. 15, 2011.
Plaintiffs Responsive Preliminary Claim Constructions and Extrinsic Evidence in U.S. Patent Nos. 6,927,069, 6,423,551, and 6,699,723, in the matter *Life Technologies Corporation, Molecular Probes, Inc. and the Regents of the University of California v. Ebioscience Inc.*, in U.S. District Court Southern District of California, Docket No. 10cv2127-IEG (NLS), dated Jun. 13, 2011.
Defendant Ebioscience, Inc's Preliminary Claim Constructions and Extrinsic Evidence in U.S. Patent Nos. 6,927,069, 6,423,551, and 6,699,723,, in the matter *Life Technologies Corporation, Molecular Probes, Inc. and the Regents of the University of California v. Ebioscience Inc.*, in U.S. District Court Southern District of California, Docket No. 10cv2127-IEG (NLS), dated May 27, 2011.
Plantiffs' Disclosure of Asserted Claims and Preliminary Infringement Contentions, *Life Technologies Corporation, Molecular Probes, Inc. and the Regents of the University of California v. Ebioscience Inc.*, in U.S. District Court Southern District of California, Docket No. 10-CV-2127-IEG, dated Mar. 16, 2011.
Premachandran et al., "The Enzymatic Sysnthesis of Thiol-Containing Polymers to Prepare Polymer-CdS Nanocomposites." Chem. Mater., 1997, 1342-1347.
Tishchenko et al., "Optical studies ZnSe-ZnS-ZnS/GaAs(1 0 0) single quantum well grown by photo-assisted vapor phase epitaxy." Solid State Communications, vol. 96, 1995, 793-798.

SEMICONDUCTOR NANOCRYSTAL PROBES FOR BIOLOGICAL APPLICATIONS AND PROCESS FOR MAKING AND USING SUCH PROBES

CROSS-REFERENCE TO RELATED APPLICATION

This application is a continuation of U.S. patent application Ser. No. 11/566,998 filed Dec. 5, 2006 which is a continuation of U.S. patent application Ser. No. 10/155,918 filed May 24, 2002 (now abandoned) which is a continuation of U.S. patent application Ser. No. 09/781,621 filed Feb. 12, 2001, now U.S. Pat. No. 6,727,065 issued Apr. 27, 2004, which is a continuation of U.S. patent application Ser. No. 09/259,982 filed Mar. 1, 1999, now U.S. Pat. No. 6,207,392 issued Mar. 27, 2001, which is a continuation-in-part of U.S. patent application Ser. No. 08/978,450 filed Nov. 25, 1997, now U.S. Pat. No. 5,990,479 issued Nov. 23, 1999, which applications are incorporated herein by reference.

The invention described herein arose in the course of, or under, Contract No. DE-AC03-SF00098 between the United States Department of Energy and the University of California for the operation of the Ernest Orlando Lawrence Berkeley National Laboratory. The Government may have rights to the invention.

BACKGROUND OF THE INVENTION

1. Field of the Invention

This invention relates to semiconductor nanocrystal probes for biological applications wherein the probes include a plurality of semiconductor nanocrystals capable of providing a detectable signal in response to exposure to energy.

2. Description of the Related Art

Fluorescent labeling of biological systems is a well known analytical tool used in modern biotechnology as well as analytical chemistry. Applications for such fluorescent labeling include technologies such as medical (and non-medical) fluorescence microscopy, histology, flow cytometry, fluorescence in-situ hybridization (medical assays and research), DNA sequencing, immuno-assays, binding assays, separation, etc.

Conventionally, such fluorescent labeling involves the use of an organic dye molecule bonded to a moiety which, in turn, selectively bonds to a particular biological system, the presence of which is then identified by excitation of the dye molecule to cause it to fluoresce. There are a number of problems with such an analytical system. In the first place, the emission of light of visible wavelengths from an excited dye molecule usually is characterized by the presence of a broad emission spectrum as well as a broad tail of emissions on the red side of the spectrum, i.e., the entire emission spectrum is rather broad. As a result, there is a severe limitation on the number of different color organic dye molecules which may be utilized simultaneously or sequentially in an analysis since it is difficult to either simultaneously or even non-simultaneously detect or discriminate between the presence of a number of different detectable substances due to the broad spectrum emissions and emission tails of the labeling molecules. Another problem is that most dye molecules have a relatively narrow absorption spectrum, thus requiring either multiple excitation beams used either in tandem or sequentially for multiple wavelength probes, or else a broad spectrum excitation source which is sequentially used with different filters for sequential excitation of a series of probes respectively excited at different wavelengths.

Another problem frequently encountered with existing dye molecule labels is that of photostability. Available fluorescent molecules bleach, or irreversibly cease to emit light, under repeated excitation ($10^4$-$10^8$ cycles of absorption/emission). These problems are often surmounted by minimizing the amount of time that the sample is exposed to light, and by removing oxygen and/or other radical species from the sample.

In addition, the probe tools used for the study of systems by electron microscopy techniques are completely different from the probes used for study by fluorescence. Thus, it is not possible to label a material with a single type of probe for both electron microscopy and for fluorescence.

It would, therefore, be desirable to provide a stable probe material for biological applications preferably having a wide absorption band and capable of providing a detectable signal in response to exposure to energy, without the presence of the large red emission tails characteristic of dye molecules (thereby permitting the simultaneous use of a number of such probe materials, each, for example, emitting light of a different narrow wavelength band) and/or capable of scattering or diffracting radiation. It would also be equally desirable to provide a single, stable probe material which can be used to image the same sample by both light and electron microscopy.

SUMMARY OF THE INVENTION

The invention comprises a semiconductor nanocrystal compound capable of linking to one or more affinity molecules to form a semiconductor nanocrystal probe. The semiconductor nanocrystal compound comprises one or more semiconductor nanocrystals and one or more first linking agents. The one or more semiconductor nanocrystals are capable of providing a detectable signal in response to exposure to energy, wherein such a response may include emission and/or absorption and/or scattering or diffraction of the energy to which the one or more semiconductor nanocrystals are exposed. In addition to or as an alternative to providing a detectable signal, the one or more semiconductor nanocrystals may transfer energy to one or more proximal structures in response to exposure to energy. The one or more first linking agents have a first portion linked to one or more semiconductor nanocrystals and a second portion capable of linking either to one or more second linking agents or to one or more affinity molecules.

The invention further comprises a semiconductor nanocrystal probe formed either by (1) linking one or more of the above described semiconductor nanocrystal compounds to one or more affinity molecules; or (2) linking one or more of the above described semiconductor nanocrystal compounds to one or more second linking agents and linking the one or more second linking agents to one or more affinity molecules, wherein the one or more affinity molecules are capable of bonding to one or more detectable substances in a material. As a result, the semiconductor nanocrystal probe, in one embodiment, is capable of absorbing energy from either a particle beam or an electromagnetic radiation source (of broad or narrow bandwidth), and is capable of emitting detectable electromagnetic radiation in a narrow wavelength band when so excited; while in another embodiment the amount of energy from either a particle beam or an electromagnetic radiation source (of broad or narrow bandwidth) which is absorbed, or scattered, or diffracted by the semiconductor nanocrystal probe, is detectable, i.e., the change in absorption, scattering, or diffraction is detectable. In yet another embodiment, the semiconductor nanocrystal probe is capable of receiving energy transferred from a proximal source and/or transferring energy to one or more proximal structures in response to exposure to energy.

The invention also comprises a process for making the semiconductor nanocrystal compound and for making the semiconductor nanocrystal probe comprising the semiconductor nanocrystal compound linked to one or more affinity molecules capable of bonding to one or more detectable substances. The semiconductor nanocrystal probe of the invention is stable with respect to repeated excitation by light, or exposure to elevated temperatures, or exposure to oxygen or other radicals.

The invention further comprises a process for treating a material, such as a biological material, to determine the presence of a detectable substance in the material, which comprises a step of contacting the material to be treated, with the semiconductor nanocrystal probe, an optional step of removing from the material the semiconductor nanocrystal probes not bonded to the detectable substance, and then a step of exposing the material to energy from, for example, either an electromagnetic radiation source (of broad or narrow bandwidth) or a particle beam. The presence of the detectable substance in the material is then determined by a step of detecting the signal provided by the semiconductor nanocrystal probe in response to exposure to energy. This may be accomplished, for example, either by measuring the absorption of energy by the semiconductor nanocrystal probe and/or detecting the emission of radiation of a narrow wavelength band by the semiconductor nanocrystal probe and/or detecting the scattering or diffraction of energy by the semiconductor nanocrystal probe, indicative (in either case) of the presence of the semiconductor nanocrystal probe bonded to the detectable substance in the material.

The invention further comprises a process for treating a material, such as a biological material with a semiconductor nanocrystal probe which is used to transfer energy to one or more proximal structures. This process comprises a step of contacting the material to be treated, with the semiconductor nanocrystal probe, an optional step of removing from the material portions of the semiconductor nanocrystal probe not bonded to the detectable substance, and then a step of exposing the material to energy from, for example, either an electromagnetic radiation source (of broad or narrow bandwidth) or a particle beam. This is followed by a step of energy transfer from the semiconductor nanocrystal probe to one or more proximal structures which may, in response to the energy transfer, either provide a detectable signal, undergo chemical or conformational changes, or transfer energy to one or more second proximal structures.

The use of the semiconductor nanocrystal probe in the treatment of a material to either provide a detectable signal or transfer energy to a proximal structure may be applied to a plurality of medical and non-medical biological applications. Exemplary applications of the semiconductor nanocrystal probe include: use as a detector of substances on the surface or interior of cells in flow cytometry; use in a plurality of methods for detecting nucleic acid sequences by hybridization, such as fluorescence in-situ hybridization (particularly when the semiconductor nanocrystal probe has been modified in a polymerase chain reaction); or use to transfer energy which may cause the release of a cytotoxic molecule or transfer of heat energy, either of which may result in death of specifically targeted cells. Another use of the semiconductor nanocrystal probe is as a precursor which is treated to synthetic steps which result in a modified semiconductor nanocrystal probe (as in the case of modification by polymerase chain reaction).

DETAILED DESCRIPTION OF THE INVENTION

Figure 1:
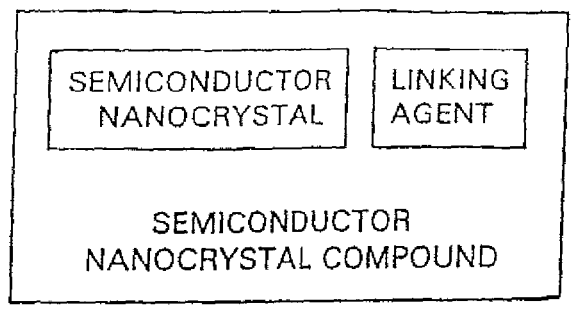
FIG. 1 is a block diagram of the semiconductor nanocrystal compound of the invention.
Figure 2:
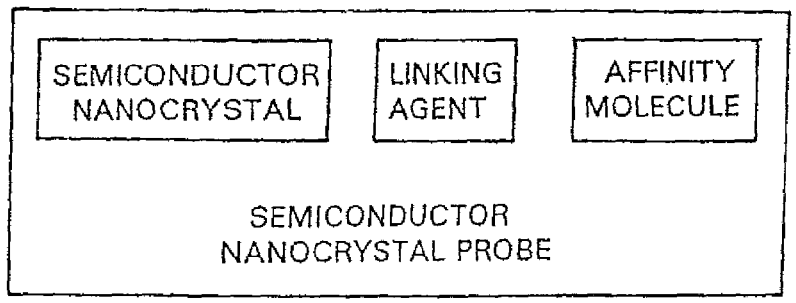
FIG. 2 is a block diagram of the semiconductor nanocrystal probe of the invention.
Figure 3:
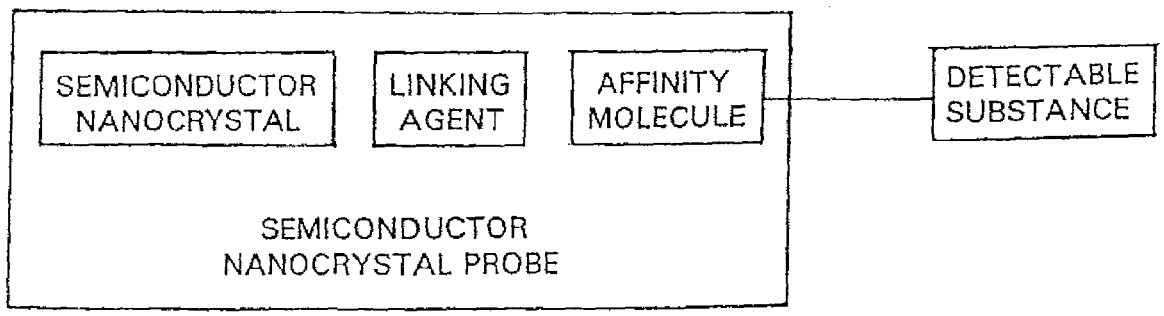
FIG. 3 is a block diagram showing the affinity between a detectable substance and the semiconductor nanocrystal probe of the invention.
Figure 4:
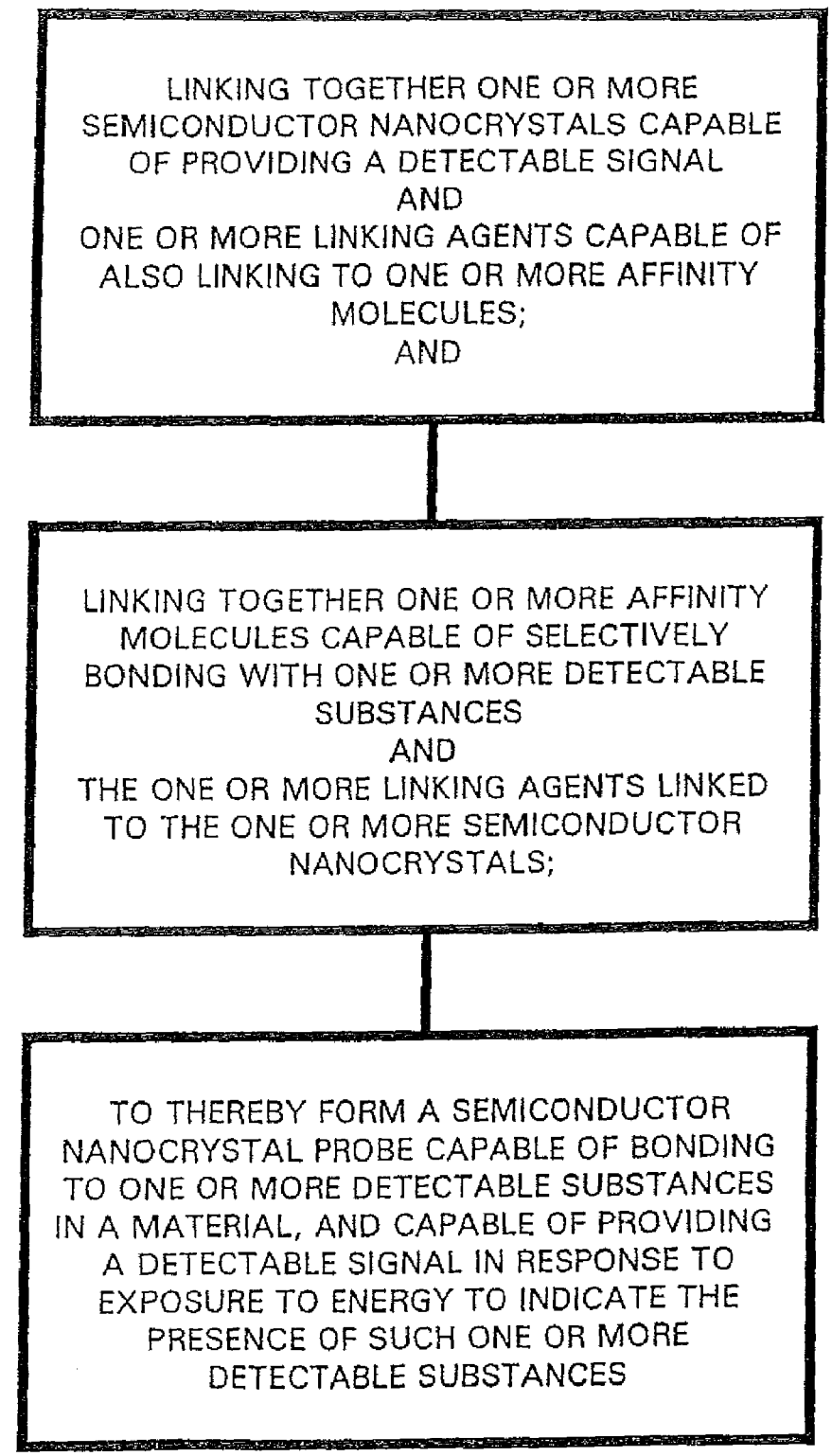
FIG. 4 is a flow sheet illustrating the process of forming the semiconductor nanocrystal probe of the invention.
Figure 5:
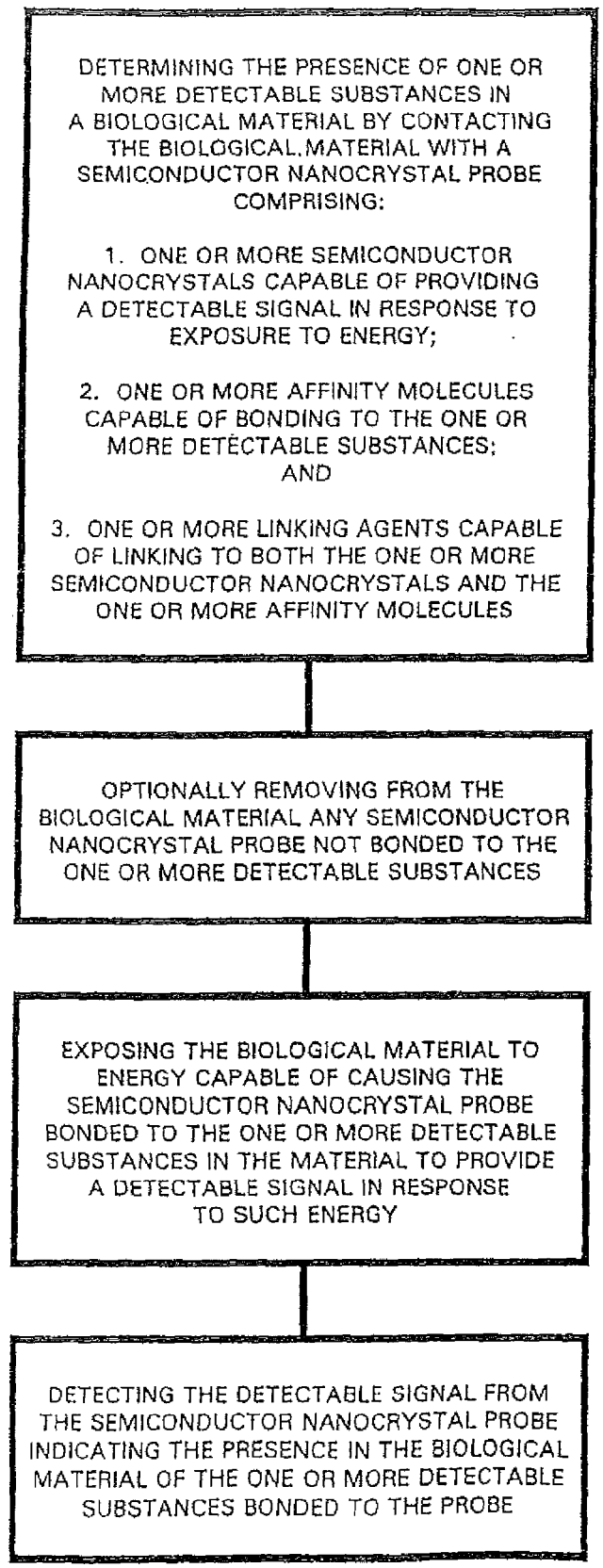
FIG. 5 is a flow sheet illustrating a typical use of the semiconductor nanocrystal probe of the invention in detecting the presence of a detectable substance in a material such as a biological material.
Figure 6:
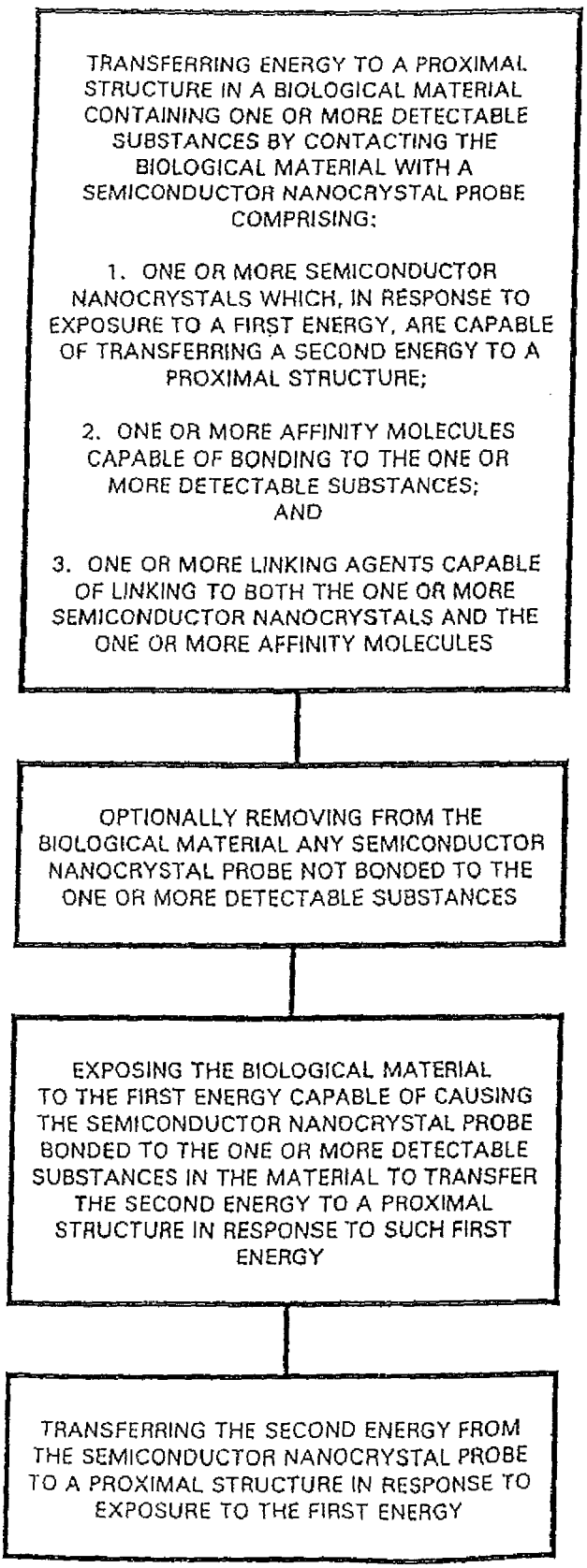
FIG. 6 is a flow sheet illustrating a typical use of the semiconductor nanocrystal probe of the invention in transferring energy to a proximal structure.

The invention comprises a semiconductor nanocrystal compound capable of linking to either one or more second linking agents or to one or more affinity molecules, and capable of providing a detectable signal in response to exposure to energy. The semiconductor nanocrystal compound, in turn, comprises: (1) one or more semiconductor nanocrystals, each capable of providing a detectable signal in response to exposure to energy; and (2) one or more first linking agents, each having a first portion linked to the semiconductor nanocrystal and a second portion capable of linking either to one or more second linking agents or to one or more affinity molecules.

The invention also comprises the above described semiconductor nanocrystal compound linked to one or more affinity molecules (through either one or more first linking agents, or through one or more second linking agents which are in turn linked to one or more first linking agents) to form a semiconductor nanocrystal probe capable of bonding to one or more detectable substances and capable of providing a detectable signal in response to exposure to energy. Treatment of a material (typically a biological material) with the semiconductor nanocrystal probe, and subsequent exposure of this treated material to energy, as described above, to determine the presence of the detectable substance within the material, will result in the semiconductor nanocrystal in the semiconductor nanocrystal probe bonded to the detectable substance providing a detectable signal. This detectable signal, such as a change in absorption and/or emission of electromagnetic radiation of a narrow wavelength band and/or scattering or diffraction may signify (in either instance) the presence in the material, of the detectable substance bonded to the semiconductor nanocrystal probe.

The invention also comprises a process for making the semiconductor nanocrystal compound, and a process for making the semiconductor nanocrystal probe comprising the semiconductor nanocrystal compound linked to one or more affinity molecules capable of bonding to one or more detectable substances.

The invention further comprises a process for treating a material, such as a biological material, to determine the presence of one or more detectable substances in the material which comprises: (1) contacting the material with the semiconductor nanocrystal probe, (2) (optionally) removing from the material the semiconductor nanocrystal probes not bonded to the detectable substance, (3) exposing the material to energy (such as the above-described electromagnetic energy source or particle beam), to which, the semiconductor nanocrystal is capable of providing a response, signifying the presence of the semiconductor nanocrystal probe bonded to the detectable substance in the material, and (4) detecting the signal provided by the semiconductor nanocrystal in the semiconductor nanocrystal probe.

The invention further comprises a process for treating a material, such as a biological material, using a semiconductor nanocrystal probe, which comprises: (1) contacting the material with the semiconductor nanocrystal probe, (2) (optionally) removing from the material the semiconductor nanocrystal probes not bonded to the detectable substance, (3) exposing the material to energy (such as an electromagnetic energy source or particle beam) capable of causing a transfer of energy from one or more semiconductor nanocrystal probes to one or more proximal structures in response to exposure to energy, and (4) transferring energy from one or more semiconductor nanocrystal probes to one or more proximal structures.

a. Definitions

By use of the terms "nanometer crystal" or "nanocrystal" herein is meant an organic or inorganic crystal particle, preferably a single crystal particle, having an average cross-section no larger than about 20 nanometers (nm) or $20 \times 10^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 angstroms).

By use of the term "semiconductor nanocrystal" is meant a nanometer crystal or nanocrystal of Group II-VI and/or Group III-V semiconductor compounds capable of emitting electromagnetic radiation upon excitation, although the use of Group IV semiconductors such as germanium or silicon, or the use of organic semiconductors, may be feasible under certain conditions.

The term "radiation," as used herein, is meant to include electromagnetic radiation, including x-ray, gamma, ultra-violet, visible, infra-red, and microwave radiation; and particle radiation, including electron beam, beta, and alpha particle radiation.

The term "energy" is intended to include electromagnetic radiation, particle radiation, and fluorescence resonance energy transfer (FRET). As used herein, the term "first energy" is meant the energy to which a semiconductor nanocrystal is exposed. Use of the term "second energy" is meant energy provided by a semiconductor nanocrystal, within a semiconductor nanocrystal compound or within a semiconductor nanocrystal probe, in response to exposure to a first energy. It should be noted that different nanocrystals, when exposed to the same "first energy", may respectively provide "second energies" which differ from one another, and the use of the term "second energy", when used in connection with a plurality of semiconductor nanocrystals will be understood to refer to either second energies which are the same or to a plurality of different second energies.

By the use of the term "energy transfer" is meant the transfer of energy from one atom or molecule to another atom or molecule by either radiative or non-radiative pathways.

The term "proximal source" is meant an atom, a molecule, or any other substance which is capable of transferring energy to and/or receiving energy transferred from another atom or molecule or any other substance.

The term "proximal structure" as used herein may be an atom, a molecule, or any other substance (e.g. a polymer, a gel, a lipid bilayer, and any substance bonded directly to a semiconductor nanocrystal probe) which is capable of receiving energy transferred from another atom or molecule or other substance (including a semiconductor nanocrystal probe).

By use of the term "a narrow wavelength band", with regard to the electromagnetic radiation emission of the semiconductor nanocrystal, is meant a wavelength band of emissions not exceeding about 40 nm, and preferably not exceeding about 20 nm in width and symmetric about the center, in contrast to the emission bandwidth of about 100 nm for a typical dye molecule, with a red tail which may extend the bandwidth out as much as another 100 nm. It should be noted that the bandwidths referred to are determined from measurement of the width of the emissions at half peak height (FWHM), and are appropriate in the range of 200 nm to 2000 nm.

By use of the term "a broad wavelength band", with regard to the electromagnetic radiation absorption of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal), which occurs near to, but at slightly higher energy than the "narrow wavelength band" of the emission. This is in contrast to the "narrow absorption band" of dye molecules which occurs near the emission peak on the high energy side, but drops off rapidly away from that wavelength and is often negligible at wavelengths further than 100 nm from the emission.

The term "detectable signal,: as used herein, is meant to include emission by the semiconductor nanocrystal of electromagnetic radiation, including visible or infrared or ultraviolet light and thermal emission; and any other signal or change in signal emanating from the semiconductor nanocrystal evidencing scattering (including diffraction) and/or absorption in response to exposure of the semiconductor nanocrystal to radiation.

By use of the term "detectable substance" is meant an entity or group or class of groups, the presence or absence of which, in a material such as a biological material, is to be ascertained by use of the semiconductor nanocrystal probe of the invention.

By use of the term "affinity molecule" is meant the portion of the semiconductor nanocrystal probe of the invention which comprises an atom, molecule, or other moiety capable of selectively bonding to one or more detectable substances (if present) in the material (e.g., biological material) being analyzed.

The use of the term "small molecule" as used herein (for either an affinity molecule or a detectable substance) is any atom or molecule, inorganic or organic, including biomolecules, having a molecular weight below about 10,000 daltons (grams/mole).

By use of the term "linking agent" is meant a substance capable of linking with one or more semiconductor nanocrystals and also capable of linking to one or more affinity molecules or one or more second linking agents.

By use of the term "first linking agent" is meant a substance capable of either (1) linking with one or more semiconductor nanocrystals, and also capable of linking to one or more affinity molecules; or (2) linking with one or more semiconductor nanocrystals and also capable of linking to one or more second linking agents.

By use of the term "second linking agent" is meant a substance capable of linking to one or more affinity molecules and also capable of linking to one or more linking agents.

Use of the term "three-dimensional structure" herein is meant to define any structure, independent of shape, which is greater than 10 nm in thickness along the three mutually perpendicular principle axes of the structure.

Use of the term "substructure" herein is meant one of two or more portions of a three-dimensional structure.

The terms "link" and "linking" are meant to describe the adherence between the one or more affinity molecules and the one or more semiconductor nanocrystals, either directly or through one or more moieties identified herein as linking agents (including second linking agents between the linking agent and the affinity molecule). The adherence may comprise any sort of bond, including, but not limited to, covalent, ionic, hydrogen bonding, van der Waals forces, or mechanical bonding, etc.

The terms "bond" and "bonding" are meant to describe the adherence between the affinity molecule and the detectable substance. The adherence may comprise any sort of bond, including, but not limited to, covalent, ionic, or hydrogen bonding, van der Waals forces, or mechanical bonding, etc.

The term "semiconductor nanocrystal compound", as used herein, is intended to define one or more semiconductor nanocrystals linked to one or more first linking agents and capable of linking to either one or more second linking agents or to one or more affinity molecules, while the term "semiconductor nanocrystal probe" is intended to define a semiconductor nanocrystal compound linked to one or more affinity molecules.

The term "glass" as used herein is intended to include one or more oxides of silicon, boron, and/or phosphorus, or a mixture thereof, as well as the further optional inclusion of one or more metal silicates, metal borates or metal phosphates therein.

b. The Semiconductor Nanocrystals

The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. As mentioned above, the use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

Formation of nanometer crystals of Group III-V semiconductors is described in commonly assigned Alivisatos et al. U.S. Pat. No. 5,751,018; Alivisatos et al. U.S. Pat. No. 5,505,928; and Alivisatos et al. U.S. Pat. No. 5,262,357, which also describes the formation of Group II-VI semiconductor nanocrystals, and which are also assigned to the assignee of this invention. Also described therein is the control of the size of the semiconductor nanocrystals during formation using crystal growth terminators. The teachings of Alivisatos et al. U.S. Pat. No. 5,751,018, and Alivisatos et al. U.S. Pat. No. 5,262,357 are each hereby specifically incorporated by reference.

In one embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1-10 monolayers in thickness. When, for example, a 1-10 monolayer thick shell of CdS is epitaxially grown over a core of CdSe, there is a dramatic increase in the room temperature photoluminescence quantum yield. Formation of such core/shell nanocrystals is described more fully in a publication by one of us with others entitled "Epitaxial Growth of Highly Luminescent CdSe/CdS Core/Shell Nanocrystals with Photostability and Electronic Accessibility", by Peng, Schlamp, Kadavanich, and Alivisatos, published in the Journal of the American Chemical Society, Volume 119, No. 30. 1997, at pages 7019-7029, the subject matter of which is hereby specifically incorporated herein by reference.

The semiconductor nanocrystals used in the invention will have a capability of absorbing radiation over a broad wavelength band. This wavelength band includes the range from gamma radiation to microwave radiation. In addition, these semiconductor nanocrystals will have a capability of emitting radiation within a narrow wavelength band of about 40 nm or less, preferably about 20 nm or less, thus permitting the simultaneous use of a plurality of differently colored semiconductor nanocrystal probes with different semiconductor nanocrystals without overlap (or with a small amount of overlap) in wavelengths of emitted light when exposed to the same energy source. Both the absorption and emission properties of semiconductor nanocrystals may serve as advantages over dye molecules which have narrow wavelength bands of absorption (e.g. about 30-50 nm) and broad wavelength bands of emission (e.g. about 100 nm) and broad tails of emission (e.g. another 100 nm) on the red side of the spectrum. Both of these properties of dyes impair the ability to use a plurality of differently colored dyes when exposed to the same energy source.

Furthermore, the frequency or wavelength of the narrow wavelength band of light emitted from the semiconductor nanocrystal may be further selected according to the physical properties, such as size, of the semiconductor nanocrystal. The wavelength band of light emitted by the semiconductor nanocrystal, formed using the above embodiment, may be determined by either (1) the size of the core, or (2) the size of the core and the size of the shell, depending on the composition of the core and shell of the semiconductor nanocrystal. For example, a nanocrystal composed of a 3 nm core of CdSe and a 2 nm thick shell of CdS will emit a narrow wavelength band of light with a peak intensity wavelength of 600 nm. In contrast, a nanocrystal composed of a 3 nm core of CdSe and a 2 nm thick shell of ZnS will emit a narrow wavelength band of light with a peak intensity wavelength of 560 nm.

A plurality of alternatives to changing the size of the semiconductor nanocrystals in order to selectably manipulate the emission wavelength of semiconductor nanocrystals exist. These alternatives include: (1) varying the composition of the nanocrystal, and (2) adding a plurality of shells around the core of the nanocrystal in the form of concentric shells. It should be noted that different wavelengths can also be obtained in multiple shell type semiconductor nanocrystals by respectively using different semiconductor nanocrystals in different shells, i.e., by not using the same semiconductor nanocrystal in each of the plurality of concentric shells.

Selection of the emission wavelength by varying the composition, or alloy, of the semiconductor nanocrystal is old in the art. As an illustration, when a CdS semiconductor nanocrystal, having an emission wavelength of 400 nm, may be alloyed with a CdSe semiconductor nanocrystal, having an emission wavelength of 530 nm. When a nanocrystal is prepared using an alloy of CdS and CdSe, the wavelength of the emission from a plurality of identically sized nanocrystals may be tuned continuously from 400 nm to 530 nm depending on the ratio of S to Se present in the nanocrystal. The ability to select from different emission wavelengths while maintaining the same size of the semiconductor nanocrystal may be important in applications which require the semiconductor nanocrystals to be uniform in size, or for example, an application which requires all semiconductor nanocrystals to have very small dimensions when used in application with steric restrictions.

c. Affinity Molecules

The particular affinity molecule forming a part of the semiconductor nanocrystal probe of the invention will be selected based on its affinity for the particular detectable substance whose presence or absence, for example, in a biological material, is to be ascertained. Basically, the affinity molecule may comprise any molecule capable of being linked to one or more semiconductor nanocrystal compounds which is also capable of specific recognition of a particular detectable substance. In general, any affinity molecule useful in the prior art in combination with a dye molecule to provide specific recognition of a detectable substance will find utility in the formation of the semiconductor nanocrystal probes of the invention. Such affinity molecules include, by way of example only, such classes of substances as monoclonal and polyclonal antibodies, nucleic acids (both monomeric and oligomeric), proteins, polysaccharides, and small molecules such as sugars, peptides, drugs, and ligands. Lists of such affinity molecules are available in the published literature such as, by way of example, the "Handbook of Fluorescent Probes and Research Chemicals", (sixth edition) by R. P. Haugland, available from Molecular Probes, Inc.

d. The Linking Agents

The semiconductor nanocrystal probe of the invention will usually find utility with respect to the detection of one or more detectable substances in organic materials, and in particular to the detection of one or more detectable substances in biological materials. This requires the presence, in the semiconductor nanocrystal probe, of an affinity molecule or moiety, as described above, which will bond the semiconductor nanocrystal probe to the detectable substance in the organic/biological material so that the presence of the detectable material may be subsequently ascertained. However, since the semiconductor nanocrystals are inorganic, they may not bond directly to the affinity molecule. In this case therefore, there must be some type of linking agent present in the semiconductor nanocrystal probe which is capable of linking the inorganic semiconductor nanocrystal to the affinity molecule in the semiconductor nanocrystal probe. The linking agent may be in the form of one or more linking agents linking one or more semiconductor nanocrystals to one or more affinity molecules. Alternatively, two types of linking agents may be utilized. One or more of the first linking agents may be linked to one or more semiconductor nanocrystals and also linked to one or more second linking agents. The one or more second linking agents may be linked to one or more affinity molecules and to one or more first linking agents.

One form in which the semiconductor nanocrystal may be linked to an affinity molecule via a linking agent is by coating the semiconductor nanocrystal with a thin layer of glass, such as silica ($SiO_x$ where x=1-2), using a linking agent such as a substituted silane, e.g., 3-mercaptopropyl-trimethoxy silane to link the nanocrystal to the glass. The glass-coated semiconductor nanocrystal may then be further treated with a linking agent, e.g., an amine such as 3-aminopropyl-tri-methoxysilane, which will function to link the glass-coated semiconductor nanocrystal to the affinity molecule. That is, the glass-coated semiconductor nanocrystal may then be linked to the affinity molecule. It is within the contemplation of this invention that the original semiconductor nanocrystal compound may also be chemically modified after it has been made in order to link effectively to the affinity molecule. A variety of references summarize the standard classes of chemistry which may be used to this end, in particular the "Handbook of Fluorescent Probes and Research Chemicals", (6th edition) by R. P. Haugland, available from Molecular Probes, Inc., and the book "Bioconjugate Techniques", by Greg Hermanson, available from Academic Press, New York.

When the semiconductor nanocrystal may be coated with a thin layer of glass, the glass, by way of example, may comprise a silica glass ($SiO_x$ where x=1-2), having a thickness ranging from about 0.5 nm to about 10 nm, and preferably from about 0.5 nm to about 2 nm.

The semiconductor nanocrystal is coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercaptopropyl-tri-methoxy silane, followed by partial hydrolysis which is followed by addition of a glass-affinity molecule linking agent such as amino-propyl trimethoxysilane which will link to the glass and serve to form a link with the affinity molecule.

When the linking agent does not involve the use of a glass coating on the semiconductor nanocrystal, it may comprise a number of different materials, depending upon the particular affinity molecule, which, in turn, depends upon the type of detectable material being analyzed for. It should also be noted that while an individual linking agent may be used to link to an individual semiconductor nanocrystal, it is also within the contemplation of the invention that more than one linking agent may bond to the same semiconductor nanocrystal and vice versa; or a plurality of linking agents may be used to link to a plurality of semiconductor nanocrystals. In addition, when first and second linking agents are used, one or more first linking agents may be linked to the same second linking agent, or more than one second linking agents may be linked to the same first linking agent.

A few examples of the types of linking agents which may be used to link to both the semiconductor nanocrystal (or to a glass coating on the nanocrystal) and to the affinity molecule in the probe are illustrated in the table below, it being understood that this is not intended to be an exhaustive list:

| Linking Agent | |
|---|---|
| Structure | Name |
| 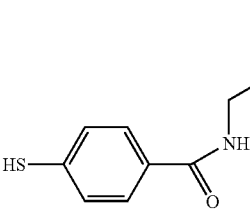 | N-(3-aminopropyl)3-mercapto-benzamide |

-continued

| Linking Agent | | |
|---|---|---|
| Structure | | Name |
| 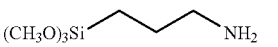 | | 3-aminopropyl-trimethoxysilane |
| 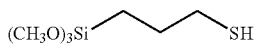 | | 3-mercaptopropyl-trimethoxysilane |
| 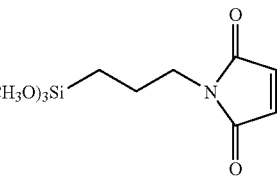 | | 3-(trimethoxysilyl)propyl-maleimide |
| 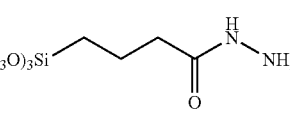 | | 3-(trimethoxysilyl)propyl-hydrazide |

It should be further noted that a plurality of polymerizable linking agents may be used together to form an encapsulating net or linkage around an individual nanocrystal (or group of nanocrystals). This is of particular interest where the particular linking agent is incapable of forming a strong bond with the nanocrystal. Examples of linking agents capable of bonding together in such a manner to surround the nanocrystal with a network of linking agents include, but are not limited to: diacetylenes, styrene-butadienes, vinyl acetates, acrylates, acrylamides, vinyl, styryl, and the aforementioned silicon oxide, boron oxide, phosphorus oxide, silicates, borates and phosphates, as well as polymerized forms of at least some of the above.

e. Compounds and Probes Having Three-Dimensional Structured Linking Agents

In one embodiment, the linking agent, including many of those described above, may be used in, or as, a three-dimensional structure which may be either organic or inorganic, and which may be either a solid (porous or non-porous) or hollow. In the prior art, the use of dye molecules embedded into latex spheres for diagnostic applications is well established. Perhaps the most common application involves selectively coloring the latex sphere using one or more dye molecules and then coating the sphere with a number of proteins of interest.

The utilization of such a three-dimensional linking agent structure (which may be most easily conceptualized as a sphere) in the compound and probe of the invention has the added benefit of permitting such a linking agent to have bonded thereto more than one semiconductor nanocrystals, as well as one or more affinity molecules (either directly or through a second linking agent). The three-dimensional linking agent structure will herein-after be described as a part of a probe (semiconductor nanocrystal, linking agent, and affinity molecule), it being understood that the structures described apply to the formation of a compound (semiconductor nanocrystal and linking agent) as well as a probe.

The advantage of a compound or probe in which one or more semiconductor nanocrystals are bonded to a three-dimensional linking agent structure lies in the ability to simultaneously use a large number of distinguishable probes. For example, when using emission of visible light as the detectable signal provided by the probe in response to exposure to radiation, multiple distinguishable probes, which each contain a single semiconductor nanocrystal of a respectively different emission color (e.g., blue probe, green probe, red probe) may be simultaneously used. Moreover, a much greater number of distinguishable probes may be simultaneously used when each probe contains a plurality of semiconductor nanocrystals, all bound to a single three-dimensional linking agent in the same probe (e.g., blue-green probe, green-red probe, blue-red probe, blue-green-red probe). Still further increases in combinations of semiconductor nanocrystals bonded to a three-dimensional linking agent structure can be achieved by varying the number of identically emitting semiconductor nanocrystals bonded to the three-dimensional linking agent in the same probe in order to provide different intensities of detectable signals (e.g. adding a second blue-emitting semiconductor nanocrystal to a blue-red probe to obtain a blue-blue-red probe, or adding another red-emitting semiconductor nanocrystal to a blue-red probe to achieve a blue-red-red probe). This further increases the total number of probes which can be simultaneously distinguished. Similar benefits can be obtained when the detectable signal or signals provided by the semiconductor nanocrystals in the probe result from scattering (including diffraction) or absorption resulting from exposure of the probe to radiation.

Similar to the incorporation of multiple semiconductor nanocrystals in a single three-dimensionally structured linking agent, multiple affinity molecules may be linked to the same three-dimensional linking agent structure to allow a plurality of detectable structures (including combinations of detectable structures) to be distinguishably and simultaneously detected by each semiconductor nanocrystal probe.

In an illustration of the use of multiple affinity molecules in each semiconductor nanocrystal probe in testing for Down's syndrome, a subset of the DNA sequences present on a particular chromosome in the human body, such as chromosome 21, may serve as the affinity molecules of a semiconductor nanocrystal probe when attached, in the form of a plurality of separate single stranded DNA fragments, to a three-dimensionally structured linking agent linked to one or more red emitting nanocrystals. A subset of the DNA sequences present on a different chromosome, such as chromosome 3, may serve as the single stranded DNA affinity molecules of another probe when similarly attached to a different three-dimensionally structured linking agent linked to one or more green emitting nanocrystals. A material comprising a total DNA sample from a human patient (or an amniocentesis sample), wherein are present one or more detectable substances in the form of single stranded DNA, may be treated with these semiconductor nanocrystal probes, resulting in the bonding of the single stranded DNA affinity molecules of the probes with the single stranded DNA detectable substances. This bonding results in the formation of double stranded DNA (in one or both probes), indicative of the presence of one or more DNA sequences (i.e., DNA sequences represented by the single stranded DNA detectable substances) in the DNA sample. This step may be followed with a step of detecting the bonding of the single stranded DNA affinity molecules with the single stranded DNA detectable substances by, for example, adding to the material, which contains the detectable substances and has been treated with the semiconductor nanocrystal probes, a double stranded DNA-binding dye molecule (which may fluoresce blue). The amount of double stranded DNA-binding dye molecules present (determined by amount of blue fluorescence) on a semiconductor nanocrystal probe, may be indicative of the amount of double stranded DNA associated with the semiconductor nanocrystal probe. Thus, the blue fluorescence from the probe containing DNA from chromosome 21 indicates the bonding of single stranded DNA affinity molecules from chromosome 21 with complementary single stranded DNA detectable substances from chromosome 21, to form double stranded DNA; and the blue fluorescence from the probe containing DNA from chromosome 3 indicates the bonding of single stranded DNA affinity molecules from chromosome 3 with complementary single stranded DNA detectable substances from chromosome 3, to form double stranded DNA.

In this test for Down's Syndrome, the semiconductor nanocrystal probe comprising single stranded DNA affinity molecules from chromosome 3, which emits green light, may serve as a reference probe, wherein the ratio of emitted green light to emitted blue light represents the reference amount of double stranded DNA present on a semiconductor nanocrystal probe. The semiconductor nanocrystal probe comprising single stranded DNA affinity molecules from chromosome 21, which emits red light, may serve as the test probe, wherein the ratio of emitted red light to emitted blue light (from the test probe) may be compared to the ratio of green light to blue light from the reference probe. A difference between the test and reference ratios may indicate extra or fewer copies of the test chromosome (chromosome 21), in this case indicating Down□s Syndrome. The number of such tests which may be simultaneously performed may be significantly increased by the use of a plurality of colors in each of a plurality of semiconductor nanocrystal probes.

As stated above, the three-dimensional linking agent structure may comprise an organic or inorganic structure, and may be a porous or non-porous solid, or hollow. When the three-dimensional linking agent structure is a porous (or non-porous) solid the semiconductor nanocrystal may be embedded therein, while the semiconductor nanocrystal may be encapsulated in a hollow three-dimensional linking agent structure. Whatever the choice of material, it will be appreciated that whenever the semiconductor nanocrystal is incorporated into the interior of the three-dimensional structure of the linking agent, e.g., into a "polymer sphere", the material comprising the linking agent must both (1) allow a first energy to be transferred from an energy source to the one or more semiconductor nanocrystals (exposing the semiconductor nanocrystal to energy), and (2) allow a second energy, provided by the one or more semiconductor nanocrystals in response to exposure to the first energy, to be either detected or transferred to a proximal structure. These transfers of energy may be accomplished by the three-dimensional linking agent being transparent to the first and/or second energies, and/or by the three-dimensional linking agent being capable of converting the first and/or second energies to a form which still enables the semiconductor nanocrystal probe to either provide a detectable signal or transfer energy to a proximal structure in response to exposure to energy.

When the three-dimensional linking agent comprises an organic material, the organic material may comprise, for example, one or more resins or polymers. The semiconductor nanocrystals may be linked to the three-dimensional linking agent by physically mixing the semiconductor nanocrystals with the resin(s) or polymer(s), or may be mixed with the monomer(s) prior to polymerization of the monomer(s) to form the polymer(s). Alternatively, the semiconductor nanocrystals may be linked to the three-dimensional linking agent by covalent bonding to either the monomer or the resin or polymer, or the semiconductor nanocrystals may be linked to the three-dimensional linking agent by adsorption (adherence to the exterior) or absorption (embedded, at least partially, into the interior). Examples of polymers which could be used as organic three-dimensional linking agents include polyvinyl acetate, styrene-butadiene copolymers, polyacrylates, and styrene-divinylbenzene copolymers. More than one polymeric chain may be present in the three-dimensional linking agent, and more than one type of polymer may be used in the three-dimensional linking agent. The final product could be a solid structure, a hollow structure, or a semi-solid porous structure.

When the three-dimensional linking agent structure comprises an inorganic material, a glass structure such as a glass sphere could comprise the transparent structure used to encapsulate one or more semiconductor nanocrystals therein. The semiconductor nanocrystals could be mixed with particles of a low melting point glass, with the mixture then heated to form the desired three-dimensional structure, e.g., a sphere. Alternatively, a porous glass such as a porous silica glass could be formed into a desired shape (or applied over a solid substrate as a porous coating), followed by incorporation of the semiconductor nanocrystals into the pores of the linking agent structure. The previously described glass-coated semiconductor nanocrystals could also be modified to provide the three-dimensional linking agent structure of this embodiment, for example by providing the glass coating over a core of such semiconductor nanocrystals or by sintering into a three-dimensional mass a plurality of such glass coated semiconductor nanocrystals comprising the same or different semiconductor nanocrystals.

An additional increase in the number of three-dimensional structured probes which can be distinguishably used may arise from placing one or more identical semiconductor nanocrystals in one of a plurality of substructures of the three-dimensionally structured probe, and organizing the various substructures of the probe in such a manner to allow a large number of uniquely identifiable probes to be formed. For example, in a single probe, the three-dimensional structured linking agent may comprise a first semiconductor nanocrystal in a first polymer comprising a first substructure, and a second semiconductor nanocrystal in a second polymer immiscible with the first substructure comprising second substructure.

One example of the arrangement of these substructures is a manner analogous to the various layers of an onion. In such a construction, different arrangements of several differently emitting semiconductor nanocrystals positioned in the various substructure layers may be distinguished from one another. Therefore, a probe containing an inner core of blue semiconductor nanocrystals, encapsulated by a first substructure layer of red semiconductor nanocrystals, which is encapsulated by a second substructure layer of green semiconductor nanocrystals may be distinguished from a probe containing an inner core of green semiconductor nanocrystals, encapsulated by a first substructure layer of blue semiconductor nanocrystals, which is encapsulated by a second substructure layer of red semiconductor nanocrystals. Thus, arranging the different substructures of the semiconductor nanocrystal probe further increases the number of distinguishable probes which may be simultaneously used.

Additionally, various probes whose substructures are assembled in different arrangements may be distinguished. For example, a probe which comprises red, green and blue semiconductor nanocrystal substructures ordered in an onion-like arrangement may be distinguished from a probe which comprises red, green, and blue semiconductor nanocrystal substructures ordered in a soccer ball-like arrangement.

Therefore, there are a number of different manipulations of the semiconductor nanocrystals in the probe which results in a very large number of distinguishable probes. These manipulations include: varying the combinations of different semiconductor nanocrystals in the probe, varying the concentrations of similar and different semiconductor nanocrystals in the probe, incorporating semiconductor nanocrystals into a plurality of substructures in the probe, and varying the arrangement of such substructures containing semiconductor nanocrystals in the probe.

The incorporation of multiple nanocrystals and/or multiple affinity molecules into a single probe can be demonstrated in the use of the probes as the stationary phase in a screen for various nucleic acid sequences, where the nucleic acid sequences in the material being analyzed constitute the mobile phase.

A plurality of probes can be prepared which may each comprise a unique combination of semiconductor nanocrystals with similar or varied emission wavelengths. Associated with each probe having a unique semiconductor nanocrystal combination is a unique combination of one or more affinity molecules comprising one or more known nucleic acid sequences. In this context, the term "nucleic acid sequence" should be understood to include single or double stranded ribonucleic acid (RNA) or deoxyribonucleic acid (DNA) molecules or chemical or isotopic derivatives thereof, each molecule comprising two or more nucleic acid monomers. A plurality of unidentified nucleic acid sequences comprising the detectable substances in a mobile phase material being analyzed may now be exposed to the above described plurality of probes, e.g. flowed over the stationary phase probes.

The detection, i.e., the identification of the nucleic acid sequences in the mobile phase bound to the probes involves two aspects. First of all the occurrence of a bonding event must be ascertained. Secondly the identification of which probe, and therefore which nucleic acid sequence or sequences (affinity molecules) of the probe, are bound to the nucleic acid sequences being analyzed. The bonding event itself may be determined by detection of a tag (e.g., a dye molecule) which has been previously attached onto all of the nucleic acid sequences being analyzed. When bonding occurs, the presence of the tag will correspond spatially to a certain probe or probes. The identification of the type of nucleic acid sequence or sequences may be determined by the detection of the signal which corresponds to a unique combination of semiconductor nanocrystals within the probe or probes involved in the bonding. For example, the probes and material being analyzed may be exposed to radiation of a type which will result in provision of detectable signals from both the dye molecule and the particular probe or probes bonded to the mobile phase nucleic acid sequences. A spatially identifiable group of signals from both the dye molecules and semiconductor nanocrystals can then be detected. The first signal, emanating from the nucleic acid sequences being identified, signifies the presence of a bonded nucleic acid sequence or sequences of any sequence type. The second detectable signal, emanating from the probe (and the semiconductor nanocrystals therein), identifies the type of nucleic acid sequence or sequences which are bonded to the probe, by virtue of the known type of nucleic acid sequence or sequences forming the affinity molecule(s) of the probe.

For example, the material being analyzed and the probes could be exposed to electromagnetic radiation from a laser light source of a frequency at which the dye is excitable and which will also excite the semiconductor nanocrystals in the probe. The resulting detectable signals from the dye molecules and the probe or probes, could be visible light emissions of one or more frequencies signifying the presence of bonded nucleic acid sequences (the light from the dye molecules) and the identity of the particular probe bonded thereto (the light from the semiconductor nanocrystals in the probe). When the spatial locations of both the dye molecule emission and the probe emission correspond, this would signify the presence of particular nucleic acid sequences bonded to particular probes known to emit light of the detected frequencies.

Thus, once bonded to one or more nucleic acid sequences from the mobile phase being analyzed, a plurality of similar or different probes may then be identified according to the unique combination of semiconductor nanocrystals present in each probe. The probes may be identified either one after the other or simultaneously. The identification of each probe then allows the identification of the unique nucleic acid sequence or combination of nucleic acid sequences bound to the probe by way of the known nucleic acid sequence comprising the affinity molecule on the surface of each probe. In this way, a large number of different nucleic acid sequences may be rapidly screened and identified.

It should be noted that while it is contemplated that each affinity molecule comprising a unique, known nucleic acid sequence or sequences will be specifically bonded to a particular unidentified nucleic acid sequence or sequences being analyzed for, thus making identification precise, other uses may be contemplated. For example, a probe could be designed having, as its affinity molecule portion, a particular known nucleic acid sequence or sequences which would be bondable to an entire group of related unidentified nucleic acid sequences, thus permitting use of the probe as a broad identification or screening agent.

f. Exposure of the Probe to Energy and Detection of Emission/Absorption/Scattering Upon exposure of the semiconductor nanocrystal probe to energy, some or all of the energy may be transferred to the semiconductor nanocrystal probe. In response to exposure to this energy, the semiconductor nanocrystal probe may provide a plurality of detectable signals. These detectable signals include (1) emission of electromagnetic radiation, (2) absorption of radiation, and (3) scattering, including diffraction, of radiation.

The emission properties of the semiconductor nanocrystal probe may be very useful in a plurality of applications. As previously mentioned, the semiconductor nanocrystal probe of the invention is capable of being excited over a broad bandwidth, yet exhibits emission in a narrow wavelength band, in contrast to the dye molecules used in the prior art. Thus electromagnetic radiation of wavelength ranging from x-ray to ultraviolet to visible to infrared waves may be used to excite the semiconductor nanocrystals in the probe. In addition, the semiconductor nanocrystals are capable of excitation from bombardment with a particle beam such as an electron beam (e-beam). Furthermore, because of the broad bandwidth at which the semiconductor nanocrystals are excitable, one may use a common excitation source for the simultaneous excitation of several probes, e.g., several probes which give off radiation at different frequencies, thus permitting simultaneous excitation and detection of the presence of several probes indicating, for example, the presence of several detectable substances in the material being examined.

Thus, for example, a laser radiation source of a given frequency, e.g., blue light, may be used to excite a first semiconductor nanocrystal probe capable of emitting radiation of a second frequency, e.g., red light, indicating the presence, in the material being illuminated, of a first detectable substance to which the particular red light-emitting semiconductor nanocrystal probe has bonded. At the same time, the same blue light laser source may also be exciting a second semiconductor nanocrystal probe (in the same material) capable of emitting radiation of a third frequency, e.g., green light, indicating the presence, in the material being illuminated, of a second detectable substance to which the particular green light-emitting semiconductor nanocrystal probe has bonded. Thus, unlike the prior art, multiple excitation sources need not be used (because of the broad bandwidth in which the semiconductor nanocrystal probe of the invention is capable of being excited), and the narrow band of emission of the specific semiconductor nanocrystals in each probe makes possible the elimination of sequencing and/or elaborate filtering to detect the emitted radiation.

Another detectable signal provided by a semiconductor nanocrystal probe in response to radiation is absorption. The presence of the semiconductor nanocrystal probe, bound to a detectable substance in a biological material, may be indicated by detection of absorption of radiation by the semiconductor nanocrystal probe. Since the semiconductor nanocrystal probe has such a wide wavelength band of absorption, detection of the semiconductor nanocrystal probe may be carried out over a wide range of wavelengths, according to the requirements of the detection process. For example, many biological materials strongly absorb visible and ultraviolet radiation, but do not strongly absorb x-ray radiation. Such a biological material containing a detectable substance may be treated with a semiconductor nanocrystal probe. Presence of the semiconductor nanocrystal probe bonded with the detectable substance may then be indicated by detection of an absorption of x-rays.

The semiconductor nanocrystal probe of the invention may also provide a detectable scattering signal in response to exposure to energy. This detectable scattering signal may be a diffraction signal. Thus, for example, presence of a detectable substance within a material treated with a semiconductor nanocrystal probe (wherein the semiconductor nanocrystal probe is bonded to the detectable substance) may be indicated by the detection of a change in the scattering cross section or in diffraction of radiation upon exposure of the material to radiation.

The semiconductor nanocrystal probe of the invention may also be used in such a way that, instead of providing a detectable signal in response to radiation, it transfers energy to a proximal structure. This proximal structure, in response to the energy transfer, may then (1) provide a detectable signal, (2) undergo chemical or conformational changes, (3) transfer energy to a second proximal structure, or (4) any combination thereof. This may be achieved by introducing the semiconductor nanocrystals and the material together by any of the above methods, and then exposing the material to energy. It should be noted that a proximal source may be used to transfer energy from the proximal source to the probe (as will be described below) in contrast to the aforesaid transfer of energy from the probe to a proximal structure.

g. General Use of the Probe

In general, the probe may be used in treating a material to determine the presence of a detectable substance by introducing the probe, for example, dispersed in a suitable carrier such as an aqueous solution (e.g., an saline solution), into the material to permit the affinity molecule of the probe to bond to the detectable substance (if such detectable substance is present in the material). After introduction of the probe into the material, unbonded probes may be optionally removed from the material, leaving only bonded probes. In either event, the material (and probes therein) may be exposed to an energy source capable of causing the probe(s) to provide a detectable signal. When the unbonded probes have not been removed, presence of the bonded probes can be determined (and distinguished from the unbonded probes) by a plurality of methods, including determining the spatial segregation of more intense detectable signals arising as a result of the localization of the bonded probes, as opposed to random dispersion (resulting in spatially random detectable signals) of the unbonded semiconductor nanocrystal probes.

As an alternative to adding the semiconductor nanocrystal probe to the material, the material may be in a carrier, such as an aqueous solution, and this material may be introduced into a compartment containing the semiconductor nanocrystal probe. The semiconductor nanocrystal probe may itself be in a carrier, or may be attached to a solid support. Presence of the detectable substance within the material may be determined by any method which is capable of indicating the bonding of the affinity molecule of the probe to the detectable substance. This may be accomplished, for example, by separating components of the material and exposing the components of the material to radiation, wherein a semiconductor nanocrystal probe, if present, may provide a detectable signal in response to exposure to radiation.

The carrier mentioned above is any type of matter that has little or no reactivity with the semiconductor nanocrystal probe, and enables storage and application of the semiconductor nanocrystal probe to the material to be treated. Such a material will often be a liquid, including many types of aqueous solutions, including biologically derived aqueous solutions (e.g. plasma from blood). Other liquids include alcohols, amines, and any other liquid which neither reacts with nor causes the dissociation of the components of the semiconductor nanocrystal probe. The carrier also comprises a substance which will not interfere with the treatment or analysis being carried out by the probe in connection with the detectable substance in the material.

A further use of the semiconductor nanocrystal probe of the invention is to provide a detectable signal in response to energy transferred from one or more spatially proximal sources. In this context, "energy transfer" is meant the transfer of energy from one atom, molecule, or any other substance (e.g. a polymer, a gel, a lipid bilayer, etc.) to another atom, molecule, or any other substance by either (1) a radiative pathway (e.g., emission of radiation by a first atom or molecule followed by scattering—including diffraction—and/or absorption of the emitted radiation by a second atom or molecule); or (2) a non-radiative pathway (e.g., fluorescence resonance energy transfer, or FRET, from a first atom or molecule to a second atom or molecule). By use of the term "proximal source" is meant an atom, a molecule, or any other substance which is capable of transferring energy to and/or receiving energy transferred from another atom or molecule or any other substance. By use of the term •spatially proximal source• is meant a proximal source spaced sufficiently close to enable energy to be transferred from a proximal source to a semiconductor nanocrystal probe. For example, in the case of FRET, a spatially proximal source comprises a proximal source spaced 10 nm or less from the semiconductor nanocrystal probe. In the case of the transfer of radioactive energy, a spatially proximal source comprises a proximal source spaced 1 µm or less from the semiconductor nanocrystal probe.

The energy transferred from a proximal source to the semiconductor nanocrystal probe may originate from the proximal source (e.g., radioactive decay of an atom or atoms within the proximal source) or may arise as a result of excitation by an energy source separate from the proximal source (e.g., excitation of a proximal source dye molecule by a laser) as will be explained below. An illustration of a radiative pathway of energy transfer is the transfer of gamma radiation from a radioactive nucleus (of the proximal source) to a semiconductor nanocrystal probe. The transferred gamma radiation may then be absorbed by the semiconductor nanocrystal probe, which, in response to absorption of the gamma radiation, provides a detectable emission signal of electromagnetic radiation. An illustration of a non-radiative pathway is activation of the semiconductor nanocrystal by a FRET from a proximal source which has been externally excited, as will be described below.

Such a spatially proximal energy transfer may be useful in measuring the concentration of the proximal source, as well as the distance of the proximal source from the probe. Spatially proximal energy transfer can also be used in the detection of an event which causes the source from which energy is transferred to become spatially proximal to the probe.

One illustration of a spatially proximal energy transfer using a semiconductor nanocrystal probe is as a concentration indicator, wherein the semiconductor nanocrystal probe, in essence, acts as an energy transfer reporter. That is, the semiconductor nanocrystal probe, for example, may provide a detectable emission signal, the strength of which is a function of the local concentration of proximal sources from which the energy is transferred. This permits the probe to be used to determine the concentration of proximal sources from which energy is transferred. A possible application of this method would be to measure the amount of a zinc finger protein, such as the RAG1 protein, synthesized by a cell during a specific length of time using a pulse-chase experiment. The cell mixture may be pulsed with an addition of radioactive zinc ions to the growth medium and may, after a specific length of time, be chased by addition of non-radioactive zinc ions in large excess (e.g., greater than 100-fold) of the radioactive zinc ions. Such a pulse-chase experiment will result in one or more radioactive zinc ions incorporated only in zinc containing proteins synthesized during the specified length of time between the pulse and the chase. The cells may then be lysed to yield a soluble cell extract comprising one or more zinc containing proteins. A semiconductor nanocrystal probe comprising an affinity molecule, such as an antibody, which selectively bonds to a particular zinc finger protein may then be added to the soluble cell extract, allowing the semiconductor nanocrystal probe to bond to the particular zinc finger protein. The concentration of the particular zinc finger protein, comprising one or more radioactive zinc ions, and acting as the proximal source from which energy is transferred, bonded to semiconductor nanocrystal probe may be indicated by a detectable signal provided by the semiconductor nanocrystal probe in response to energy transferred from the radioactive zinc ion of the bonded particular zinc finger protein.

Another illustration of a spatially proximal energy transfer using the semiconductor nanocrystal probe is as a distance indicator. The strength of the detectable signal, for example, an emission, from a semiconductor nanocrystal probe is a function of the distance (provided that the distance is less than about 1 μm) between the semiconductor nanocrystal probe and the proximal source from which energy is transferred. Therefore, the detectable signal provided by the semiconductor nanocrystal probe may serve as an indicator of the distance between the semiconductor nanocrystal probe and the proximal source from which energy is transferred. A possible application for this is in the ability to determine spatial proximity of individual subunits of a multi-subunit complex within a cell, such as a transcriptional initiation complex, a ribosome, a lipid-lipoprotein complex, etc. For example, a semiconductor nanocrystal probe may bond with a protein subunit of a ribosome, while a RNA subunit of the ribosome may be labeled with a radioactive phosphorous atom, which serves as the proximal source from which energy is transferred (in this illustration, the energy transferred from the proximal source to the semiconductor nanocrystal probe originates from the proximal source). Since the strength of the emission of a detectable signal is a function of the distance between the semiconductor nanocrystal probe and the proximal source from which energy is transferred, the signal provided by the semiconductor nanocrystal probe bonded to the protein subunit indicates the approximate distance between the portion of the protein subunit bonded to the semiconductor nanocrystal probe and the portion of the RNA which contains the radioactive phosphorus atom from which the energy is transferred.

The spatially proximal energy transfer use of the semiconductor nanocrystal probe also may be utilized to detect the occurrence of an event. This event, for example, may cause the source from which energy is transferred to be located spatially proximal to the semiconductor nanocrystal probe. Since the detectable signal is a function of the distance between the proximal source from which energy is transferred and the semiconductor nanocrystal probe, the signal provided by the semiconductor nanocrystal probe may yield information reflective of an event which causes the source to be sufficiently proximal (less than about 10 nm) to enable energy to be transferred from the proximal source to the semiconductor nanocrystal probe. By way of illustration, a semiconductor nanocrystal probe may bond with a thyroid hormone receptor molecule. A thyroid hormone such as thyroxine may be labeled with a radioactive iodine atom, which serves as the source from which energy is transferred. An event which causes the thyroxine to bond to the thyroid hormone receptor will also cause the radioactive iodine atom in the thyroxine to be spatially proximal to the semiconductor nanocrystal probe. Therefore, this bonding event will cause energy to be transferred from the radioactive iodine atom to the semiconductor nanocrystal probe which may provide a detectable signal in response to the energy transfer. The detectable response will thus serve as an indicator of the event of thyroxine bonding to the thyroid hormone receptor.

The energy transferred from one or more proximal sources to one or more semiconductor nanocrystal probes may either originate from the proximal source (as in the example of radioactive decay of an atom or atoms within the proximal source), or may arise as a result of excitation of the one or more proximal sources by an energy source separate from the proximal sources. By use of the term •energy source separate from the proximal source• is meant any source of radiation or any other energy which transfers energy to the proximal source. The energy source separate from the one or more proximal sources may either be spatially distant or spatially proximal to the proximal source from which energy is transferred to the semiconductor nanocrystal probe. Thus, the energy may be transferred from a spatially distant energy source such as, for example, a laser or particle beam; or the energy may be transferred from a second spatially proximal source from which second proximal source the energy transferred may either originate, or arise as a result of excitation by an energy source separate from the second proximal source. For example, a laser beam may be used to excite a second proximal source, the second proximal source then excites the first proximal source, and the first proximal source excites the semiconductor nanocrystal probe; or a second proximal source may be a radioactive atom which excites the first proximal source which excites the semiconductor nanocrystal probe. It will be understood that more than two proximal energy sources can be utilized to transfer energy in a cascading effect. Included in pathways of excitation of the proximal source by a separate source is the case where the separate source is a particle beam which, when the proximal source is exposed to the particle beam, may cause a nuclear event in the proximal source. The proximal source may then transfer energy to the semiconductor nanocrystal probe as a result of the nuclear event caused by exposure of the proximal source to the particle beam.

When the excitation of the proximal source arises as a result of energy transferred from a separate energy source (e.g., a laser beam) the energy transfer from the proximal source to the semiconductor nanocrystal probe may be accomplished by FRET, as previously mentioned. Thus, an energy source separate from the proximal source, such as a laser, may excite a proximal source. The proximal source, as a result of relaxing from an excited state, may transfer energy via fluorescence resonance energy transfer to the semiconductor nanocrystal probe when the proximal source is less than about 10 nm from the semiconductor nanocrystal probe. The semiconductor nanocrystal probe may then provide a detectable signal such as electromagnetic radiation in response to the energy transfer from the proximal molecule. An illustration of both the excitation of the proximal molecule by an energy source separate from the proximal energy source and the use of FRET as the pathway of energy transfer from the proximal source to the probe may be derived from the previously described ribosomal example. In contrast to the previous example which used an RNA subunit of the ribosome labeled with a radioactive phosphorus atom as the proximal source, a dye molecule may be attached to the RNA subunit instead of the radioactive phosphorous atom. The proximal source RNA subunit with attached dye molecule may then be excited by a separate source, for example a laser beam. The excited proximal source RNA subunit may transfer energy to a semiconductor nanocrystal probe by way of a non-radiative energy transfer pathway such as FRET, which may provide a detectable signal in response to the energy transferred from the proximal source RNA subunit.

The use of a proximal source to transfer energy to a semiconductor nanocrystal probe may be modified in such a way as to enable a proximal source to transfer energy to a plurality of semiconductor nanocrystal probes. By way of illustration, in the previous example using an RNA molecule labeled with a dye molecule as the proximal molecule, a plurality of RNA proteins may be labeled, each with a differently emitting semiconductor nanocrystal probe. Fluorescence resonance energy may be transferred from the dye molecule to one or more of the differently emitting semiconductor nanocrystal probes. The detectable signals provided by the one or more differently emitting semiconductor nanocrystal probes may then signify proximity between the dye and the one or more semiconductor nanocrystal probes.

Since semiconductor nanocrystals of specific wavelength emission may be selected for use in a particular probe, a semiconductor nanocrystal probe may be exposed to, for example, a radioactive atom emitting gamma radiation from a proximal source, and the wavelength of the emission from the semiconductor nanocrystal probe, in response to exposure to gamma radiation from the proximal source, may be selected to be ultraviolet radiation, according to the nature of the semiconductor nanocrystal within the semiconductor nanocrystal probe. Alternatively, the wavelength of the emission of the semiconductor nanocrystal in response to exposure to, for example, gamma radiation from the proximal source may be selected to be red light. The ability to provide multiple and selectable different emissions in response to exposure to the identical radiation allows a plurality of differently emitting semiconductor nanocrystal probes to be used simultaneously.

The simultaneous use of a plurality of probes which each emit different wavelengths of electromagnetic radiation can be used, for example, in a configuration where proximity between a specific semiconductor nanocrystal probe and a source from which energy is transferred to the semiconductor nanocrystal probe may be determined by the specific wavelength of the emission from the semiconductor nanocrystal probe. For example, three semiconductor nanocrystal probes which differ in the visible light they emit (e.g., blue, green, and red emitting semiconductor nanocrystal probes) could be attached to portions of an association of molecules (e.g., an organelle). Presence of a certain molecule with a radioactive atom attached (therefore acting as the proximal source) in proximity to one specific semiconductor nanocrystal probe results in emission of a specific color, indicating proximity between the certain molecule and the specific semiconductor nanocrystal probe and its associated affinity molecule.

Similar to the use of multiple semiconductor nanocrystals, it is possible to use multiple proximal sources capable of transferring energy to one or more semiconductor nanocrystal probes.

Similar to the process in which energy is transferred from one or more proximal sources to one or more semiconductor nanocrystal probes, energy may also be transferred from one or more semiconductor nanocrystal probes to one or more proximal structures in response to exposure of the semiconductor nanocrystal probe to energy. The term "proximal structure" as used herein may be an atom, a molecule, or any other substance (e.g. a polymer, a gel, a lipid bilayer, and any substance bonded directly to a semiconductor nanocrystal probe) which is capable of receiving energy transferred from another atom or molecule or other substance (including a semiconductor nanocrystal probe). The proximal structure, in response to the energy transferred from the semiconductor nanocrystal probe, may (1) provide a detectable signal, (2) undergo chemical and/or conformational changes, (3) transfer energy to one or more second proximal structures, or (4) any combination thereof. As used herein, a "second proximal structure" is a proximal structure to which energy is transferred from a first proximal structure which has received energy from a semiconductor nanocrystal probe. The second proximal structure, in response to the energy transferred from the first proximal structure may (1) provide a detectable signal, (2) undergo chemical and/or conformational changes, (3) transfer energy to one or more third proximal structures (where a "third proximal structure" is one to which energy has been transferred from a second proximal structure), or (4) any combination thereof. It will be understood that the transfer of energy between proximal structures may be further extended beyond a third proximal structure in a cascading effect.

An illustration of the use of a semiconductor nanocrystal probe to transfer energy to a proximal structure which provides a detectable signal is as follows. A semiconductor nanocrystal probe may be used to provide an emission of a narrow wavelength band in the blue region of visible light in response to excitation over a broad wavelength band of radiation. When this semiconductor nanocrystal probe is spatially proximal to a dye molecule (the dye molecule herein is acting as the proximal structure), the dye molecule may then become excited upon transfer of energy from the semiconductor nanocrystal probe. The excited dye molecule may then be capable of providing a detectable red light emission in response to excitation by the energy transfer from the semiconductor nanocrystal.

An illustration of the use of a semiconductor nanocrystal probe to transfer energy to a proximal structure which, in response to the energy transferred from the semiconductor nanocrystal probe, undergoes chemical changes, is the use of semiconductor nanocrystals to break covalent bonds. A semiconductor nanocrystal probe may be exposed to energy, and may then transfer energy to a proximal structure in response to the exposure to energy. The energy transferred may be, for example, electromagnetic radiation which is capable of inducing a photolytic cleavage (or photolysis) of a covalent bond in a proximal structure. This action of photolysis may also result in the detachment of a portion of the proximal structure. This detached portion of the proximal structure may be, for example, a molecule used for therapeutic purposes such as a molecule with cytotoxic properties. This use of the semiconductor nanocrystal probe to break covalent bonds may be controlled in a dosage specific manner, according to the extent of exposure of the semiconductor nanocrystal probe to radiation. This control of the exposure of the semiconductor nanocrystal probe to radiation may result in control of the energy transferred to the proximal structure, which controls the photolytic cleavage of the covalent bond, and ultimately controls the detachment of the portion of the proximal structure. Additionally, the portion of the proximal structure may be detached in a spatially specific manner, according to the specificity of the one or more affinity molecules of the semiconductor nanocrystal probe.

This use of the semiconductor nanocrystal probe to break covalent bonds in the proximal structure may be particularly effective when the energy transferred to the semiconductor nanocrystal probe has a long wavelength which is transparent to the material surrounding the semiconductor nanocrystal probe. For example, a semiconductor nanocrystal probe may be exposed to electromagnetic radiation from a laser which emits at a wavelength of 700 nm (infrared radiation). Materials such as biological materials absorb very little radiation at 700 nm, but a semiconductor nanocrystal probe may absorb radiation at 700 nm. It is common for photolytic cleavages to require ultraviolet radiation for activation. An advantage of the semiconductor nanocrystal probe of the invention is that it may be made to transfer energy corresponding to ultraviolet radiation when exposed to infrared radiation as a result of a process termed two-photon absorption. Two-photon absorption may occur when a semiconductor nanocrystal probe is exposed to radiation in such a way that it simultaneously absorbs two quanta of radiation (i.e., two photons), and the resultant level of excitation of the semiconductor nanocrystal probe is twice as large as the level of excitation the semiconductor nanocrystal probe would have if it had absorbed a single quantum of radiation. By the physical relationship between energy and wavelength of radiation ($E=hc/\lambda$, where E is energy, h and c are constants, and $\lambda$ is wavelength), a level of excitation, corresponding to two quanta of a first type of radiation with a certain wavelength, would correspond to the level of excitation caused by absorption of a single quantum of a second type of radiation with a wavelength half that of the first type of radiation. Thus, if a semiconductor nanocrystal probe simultaneously absorbs two photons with wavelength of 700 nm, the excitation level of the semiconductor nanocrystal probe will be the same as the excitation level of a semiconductor nanocrystal probe which absorbs a single photon with a wavelength of about 350 nm (ultraviolet radiation). A semiconductor nanocrystal probe which has been excited by two-photon absorption may thus transfer energy, for example, by emitting electromagnetic radiation with a shorter wavelength than the wavelength of the radiation to which the semiconductor nanocrystal probe was exposed.

As an illustration of the use of this two-photon absorption, a semiconductor nanocrystal probe, comprising one or more affinity molecules which may specifically bond to one or more detectable substances representative of the presence of a cancerous cell or tissue, may be exposed to radiation from an infrared laser emitting at 700 nm. This semiconductor nanocrystal probe may then be excited by the infrared radiation (through the process of two-photon absorption), and may then emit ultraviolet radiation (which has a shorter wavelength—e.g. about 350 nm). This emitted radiation in the ultraviolet range (or energy transferred by some other process, such as by FRET) may then cause a photolytic cleavage in a proximal structure, which results in a cytotoxic molecule being detached from the proximal structure and acting as a toxin to the cancerous cell or tissue.

Another illustration of the response to the energy transferred from the semiconductor nanocrystal probe to the proximal structure resulting in the proximal structure undergoing chemical or conformational changes may result when the energy transferred from the semiconductor nanocrystal probe to the proximal structure is heat energy. This transfer of heat energy may result in a conformational change such as the heat-induced denaturation of a protein. A semiconductor nanocrystal probe may be able to absorb radiation which is not absorbed by the material surrounding the semiconductor nanocrystal probe. In response to exposure of the semiconductor nanocrystal probe to radiation, the semiconductor nanocrystal probe may transfer heat energy to a proximal structure, resulting in a local heating of structures proximal to the semiconductor nanocrystal probe. In response to this local heating, the proximal structure may (1) undergo a chemical or conformational change, and/or (2) transfer energy to a second proximal structure. Thus, exposure of a material to radiation (to which radiation the material is transparent) may result in local heating within the material. The heat energy transferred from the semiconductor nanocrystal to the proximal structure may then result in chemical or conformational changes in the proximal structure, and/or some or all of the heat energy may be transferred to a second proximal structure which itself could undergo chemical or conformational changes and/or transfer some or all of the heat energy to a third proximal structure, and so on. As in the example of the photolytically detached cytotoxic molecule, use of the semiconductor nanocrystal probe to cause transfer of heat energy may be controlled in a dosage specific manner, according to the extent of exposure of the semiconductor nanocrystal probe to radiation. Additionally, the heat energy may be transferred in a spatially specific manner, according to the specificity of the one or more affinity molecules of the semiconductor nanocrystal probe.

The amount of heat energy transferred to a proximal structure from a semiconductor nanocrystal probe in response to exposure to radiation may be enough to generate a large amount of local heating due to the high degree of stability and the large extinction coefficients characteristic of nanocrystals. In a specific example of the extent of local heating which may occur, when semiconductor nanocrystals (which emit infrared radiation) are present in a tissue at a concentration of about 0.0001 grams of semiconductor nanocrystals per gram of tissue, and these nanocrystals are exposed to an ultraviolet excitation source (or a two photon absorption source capable of exciting with an ultraviolet excitation energy), the heat energy transferred by these semiconductor nanocrystals over 1,000,000 photocycles (about one second of exposure to a saturating laser) in response to exposure to radiation may cause the tissue to increase in temperature by about 25° C. This large amount of local heating may be, for example, great enough to kill local cells and tissue; and therefore this use of the semiconductor nanocrystal probe to transfer heat energy may be applied to the treatment of cancerous cells or other nefarious cells and tissues.

Energy transfer from one or more semiconductor nanocrystal probes to one or more proximal structures may take place in a manner similar to any of the previously described transfers of energy from one or more proximal sources to one or more semiconductor nanocrystal probes. Therefore, a semiconductor nanocrystal probe may transfer energy to a proximal structure by way of radiative or non-radiative (e.g., FRET) pathways. The energy transferred from a semiconductor nanocrystal probe to a proximal structure by a radiative pathway may include particle and electromagnetic radiation. The energy transfer from a semiconductor nanocrystal probe to a proximal structure may occur as a result of energy transferred from an energy source separate from the semiconductor nanocrystal probe. This energy source separate from the semiconductor nanocrystal probe may either be a spatially distant energy source such as, for example, a laser or particle beam; or the energy may be transferred from a spatially proximal source, as previously discussed. This includes, for example, a spatially distant energy source which may transfer energy to a spatially proximal source, which may transfer energy to a semiconductor nanocrystal probe, which may transfer energy to a proximal structure.

Prior to using a semiconductor nanocrystal probe in a process comprising exposure of the semiconductor nanocrystal probe to energy, the semiconductor nanocrystal probe may be used as a precursor which may be subjected to further synthetic steps. These further synthetic steps may result in formation of a modified semiconductor nanocrystal probe which has a different affinity molecule than the affinity molecule of the precursor semiconductor nanocrystal probe. For example, a semiconductor nanocrystal probe, having one or more nucleic acid monomers as its affinity molecule portion, may serve as a precursor (primer) in a process for synthesizing DNA in large amounts, such as polymerase chain reaction (PCR); and the final PCR product may be a modified semiconductor nanocrystal probe having an affinity molecule with a greater number of nucleic acid monomers than the affinity molecule of the precursor semiconductor nanocrystal probe. The synthetic steps to which the semiconductor nanocrystal probe may be subjected include, for example, any method of nucleic acid synthesis (by use of the term, •nucleic acid synthesis• it is meant any enzymatic process of synthesizing nucleic acid strands using nucleic acid monomers). In any such nucleic acid synthesis (including the above PCR case), the precursor semiconductor nanocrystal probe is understood to comprise one or more nucleic acid strands, each comprising a number of nucleic acid monomers sufficient to allow the precursor semiconductor nanocrystal to be used as a primer in a nucleic acid synthesis reaction such as PCR (the nucleic acid strands often having from 1 to about 50 nucleic acid monomers) as the one or more affinity molecules portion of the semiconductor nanocrystal probe. The term "nucleic acid strand" should be understood to include a plurality of single or double stranded ribonucleic acid (RNA) or deoxyribonucleic acid (DNA) molecules or chemical or isotopic derivatives thereof, each molecule comprising two or more nucleic acid monomers. This nucleic acid strand affinity molecule portion may be modified by extending the nucleic acid strands by addition of nucleic acid monomers according to the desired sequence of the nucleic acid synthesis (chains may vary in length from 1 more nucleic acid monomer than the precursor, or primer, to as much as 500,000 nucleic acid monomers, or more if desired). This modified semiconductor nanocrystal probe is understood to have all of the properties and potential uses of any semiconductor nanocrystal probe.

That is, the modified semiconductor nanocrystal probe is capable of bonding with one or more detectable substances, and is capable of providing a detectable signal in response to exposure to energy. This may include, for example, use of the modified semiconductor nanocrystal probe (comprising an affinity molecule with a modified DNA sequence) as a fluorescent marker in a plurality of nucleic acid based assays, including DNA sequencing assays and hybridization assays such as fluorescence in-situ hybridization and comparative genomic hybridization.

Another advantage of the semiconductor nanocrystal probe (or a semiconductor nanocrystal compound) of the invention is in any process which involves elevated temperatures. As used herein, "elevated temperatures" are understood to include temperatures from room temperature (about 25° C.) up to the temperature at which the particular semiconductor nanocrystal probe undergoes thermal degradation. Typically this may occur at temperatures of about 150° C. or even as low as 100° C. Because of the high degree of thermal stability of the semiconductor nanocrystals, semiconductor nanocrystal probes (or semiconductor nanocrystal compounds) may withstand use at elevated temperatures, including use in processes which comprise thermal cycling steps (i.e., processes which comprise one or more steps in which the temperature is cycled between a low temperature and a high temperature, such as the aforementioned PCR). For example, as discussed above, a precursor semiconductor nanocrystal probe may be used in PCR, which requires multiple steps in which the temperature is cycled between a low temperature (the DNA synthesis step) and a high temperature (the DNA strand separation step). The high temperature of the PCR reaction mixture may be about $95_1$ C, a temperature at which many dye molecules degrade. The thermal stability properties of the semiconductor nanocrystal probe enable it to withstand the thermal cycling of PCR.

In addition to the use of semiconductor nanocrystal probes in PCR, the advantage of the high degree of thermal stability of the semiconductor nanocrystal probes may be applied to any other processes which may require elevated temperatures, such as use in heat shock methods, or methods using thermostable organisms or biomolecules derived from thermostable organisms.

An illustration of the simultaneous use of a plurality of different semiconductor nanocrystal probes is when a plurality of semiconductor nanocrystal probes are used in flow cytometry analysis. Flow cytometry, as used in the prior art, involves contacting a material, containing cells, with one or more dyes, or dye conjugated affinity molecules, which are capable of detecting certain molecules or substances on the surface or interior of those cells. The presence of the dye molecules on the surface or interior of a cell (and, hence, the presence of the certain molecule with which the dye interacts) is detected by flowing the material through a compartment which is transparent to both the energy to which the material is exposed, and to the detectable signal provided by the dye in response to exposure to energy. As the cells are within the transparent compartment, the cells are exposed to energy, such as electromagnetic radiation, which is capable of being absorbed by the dye. The dye, as a result of exposure to the electromagnetic radiation, emits a detectable signal, such as electromagnetic radiation of a different wavelength than that to which the material is exposed. When a plurality of dyes are used to indicate the presence of a plurality of substances on the surface or interior of the cells, the material containing the cells may be flowed through a plurality of transparent compartments, and the presence of a plurality of different dyes may be tested one at a time (i.e. consecutively) or a few at a time (maximum of three simultaneous detections).

In accordance with the invention, instead of using a dye molecule, a material containing cells may alternatively be contacted with a semiconductor nanocrystal probe (actually a plurality of probe, but all providing the same detectable signal in response to energy). The semiconductor nanocrystal probe may bond to one or more detectable substances, if any are present, on the surface or interior of the cells, to which the affinity molecules of the semiconductor nanocrystal probe are capable of bonding. Detection of the presence of the semiconductor nanocrystal probe (and hence, the presence of one or more specific detectable substances to which the semiconductor nanocrystal probe is bonded) may take place by first contacting the material containing the cells with the semiconductor nanocrystal probe. The material is then flowed through a transparent compartment wherein the material is exposed to energy such as, for example, ultraviolet laser radiation. The presence of the semiconductor nanocrystal probe may be indicated by a detectable signal such as, for example, emission of red light, provided by the semiconductor nanocrystal probe in response to exposure to energy. Detection of the detectable signal provided by the semiconductor nanocrystal probe, therefore, may indicate the presence of one or more detectable substances, on the surface or interior of cells, to which the semiconductor nanocrystal probe is bonded.

Use of a plurality of groups of semiconductor nanocrystal probes (each of which groups provide the same detectable signal in response to exposure to energy) may be conducted in a manner similar to the above use of a single semiconductor nanocrystal probe. The material containing the cells may be contacted with a plurality of semiconductor nanocrystal probes, and the material is then flowed through a plurality of transparent compartments. In each compartment, the presence of a specific semiconductor nanocrystal probe bonded to one or more detectable substances may be indicated by a particular detectable signal provided by the specific semiconductor nanocrystal probe. However, unlike the prior art, since each separate semiconductor nanocrystal probe is capable of producing a detectable signal (in response to energy) which is distinguishable from the detectable signals produced by other semiconductor nanocrystal probes which have been exposed to the same energy, the presence of more than one semiconductor nanocrystal probe, each bonded to one or more different detectable substances, may be simultaneously detected in a single compartment.

Furthermore, methods of using one or more semiconductor nanocrystal probes to detect one or more detectable substances on the surface or interior of cells may not require flowing the material through a transparent compartment, thereby extending the use of the semiconductor nanocrystal probes to any cytometric method (i.e. any method which is used to detect the presence of detectable substances on the surface or interior of cells). Instead of flowing the cell-containing material through a transparent compartment, the presence of one or more of a plurality of semiconductor nanocrystal probes bonded to the cells may be detected by any technique capable of detecting the signals from the different semiconductor nanocrystal probes in a spatially sensitive manner. Such spatially sensitive detection methods include, for example, confocal microscopy and electron microscopy, as well as the aforementioned flow cytometry.

The following examples will serve to further illustrate the formation of the semiconductor nanocrystal probes of the invention, as well as their use in detecting the presence of a detectable substance in a material such as a biological material.

Example 1

To illustrate the formation of the semiconductor nanocrystal compound (comprising the semiconductor nanocrystals linked to a linking agent) 20 ml. of a 5 mM solution of (4-mercapto)benzoic acid was prepared with a pH of 10 using $(CH_3)_4NOH.5H_2O$. 20 mg of tris-octylphosphine oxide coated CdSe/CdS core/shell nanocrystals were added to the solution and stirred until completely dissolved. The resultant nanocrystal/linking agent solution was heated for 5 hours at 50-60° C. and then concentrated to a few ml by evaporation. Then an equal volume of acetone was added and the nanocrystals precipitated out of solution homogeneously. The precipitate was then washed with acetone, dried, and then can be stored.

The semiconductor nanocrystal compound prepared above can be linked with an appropriate affinity molecule to form the semiconductor nanocrystal probe of the invention to treat a biological material to determine the presence or absence of a detectable substance. That is, the semiconductor nanocrystal compound prepared above can be linked, for example, with avidin or streptavidin (as the affinity molecule) to form an semiconductor nanocrystal probe to treat a biological material to ascertain the presence of biotin; or the semiconductor nanocrystal compound prepared above can be linked with anti-digoxigenin to form an semiconductor nanocrystal probe to treat a biological material to ascertain the presence of digoxigenin.

Example 2

To illustrate the formation of a semiconductor nanocrystal compound (comprising silica coated semiconductor nanocrystals linked to a linking agent) 200 μl of 3-(mercaptopropyl)-trimethoxysilane and 40 μl of 3-(aminopropyl)-trimethoxysilane were added to 120 ml of anhydrous 25% (v/v) dimethylsulfoxide in methanol. The pH of this solution was adjusted to 10 using 350 μl of a 25% (w/w) solution of $(CH_3)_4)NOH$ in methanol. 10 mg of CdS or ZnS or ZnS/CdS coated CdSe nanocrystals were dissolved into this solution (prepared, in the case of CdS, by a technique such as the technique described in the aforementioned Peng, Schlamp, Kadavanich, and Alivisatos article; or in the case of ZdS, by the technique described by Dabbousi et al. in "(CdSe)ZnS Core-Shell Quantum Dots: Synthesis and Characterization of a Size Series of Highly Luminescent Nanocrystals," Journal of Physical Chemistry B 101 pp 9463-9475, 1997), stirred to equilibrate for several hours, diluted with 200 ml of methanol with 150 μl of a 25% (w/w) solution of $(CH_3)_4NOH$ in methanol, then heated to boiling for 30 minutes. This solution was then cooled and mixed with a 200 ml solution of 90% (v/v) methanol, 10% (v/v) water, containing 1.0 ml of 3-(trihydroxysilyl)propyl methylphosphonate, monosodium salt (42% w/w solution in water) and 40 μl of 3-(aminopropyl)trimethoxysilane. This solution was stirred for two hours, then heated to boiling for fewer than five minutes, then cooled. Once cool, a solution of 4 ml of chlorotrimethylsilane in 36 ml methanol, the pH of which had been adjusted to 10 using solid $(CH_3)_4NOH.5H_2O$, was mixed with the solution and stirred for one hour. This solution was then heated to boiling for 30 minutes, cooled to room temperature and stirred for several hours more. The solvent was evacuated partially in vacuo at 60° C. This solution can be precipitated to an oily solid with acetone. The semiconductor nanocrystal compound may then be redissolved in water, and in a variety of buffer solutions to prepare it for linking it to an affinity molecule to form the semiconductor nanocrystal probe of the invention to treat a biological material to determine the presence or absence of a detectable substance.

Thus, the invention provides an semiconductor nanocrystal probe containing a semiconductor nanocrystal capable, upon excitation by either electromagnetic radiation (of either narrow or broad bandwidth) or particle beam, of emitting electromagnetic radiation in a narrow wavelength band and/or absorbing energy and/or scattering or diffracting said excitation, thus permitting the simultaneous usage of a number of such probes emitting different wavelengths of electromagnetic radiation to thereby permit simultaneous detection of the presence of a number of detectable substances in a given material. The probe material is stable in the presence of light or oxygen, capable of being excited by energy over a wide spectrum, and has a narrow band of emission, resulting in an improved material and process for the simultaneous and/or sequential detection of a number of detectable substances in a material such as a biological material.

Having thus described the invention what is claimed is:

1. A semiconductor nanocrystal composition, comprising:
   a) a core comprising a first semiconductor material;
   b) a core-overcoating shell comprising a second semiconductor material, wherein the core and the core-overcoating shell form a core/shell nanocrystal; and
   c) an encapsulating net surrounding the core/shell nanocrystal.

2. The semiconductor nanocrystal composition of claim 1, wherein said semiconductor nanocrystal composition is water-soluble.

3. The semiconductor nanocrystal composition of claim 1, wherein said semiconductor nanocrystal composition has a narrow emission wavelength band.

4. The semiconductor nanocrystal composition of claim 3, wherein said narrow emission wavelength band does not exceed 40 nm in width when measured at full width half maximum.

5. The semiconductor nanocrystal composition of claim 3, wherein said narrow emission wavelength band does not exceed about 20 nm in width when measured at full width half maximum.

6. The semiconductor nanocrystal composition of claim 1, wherein said encapsulating net comprises one or more linking agents capable of linking said core/shell nanocrystals to one or more affinity molecules.

7. The semiconductor nanocrystal composition of claim 6, wherein said one or more linking agents are polymerizable.

8. The semiconductor nanocrystal composition of claim 6, wherein said one or more linking agents comprise a thiol moiety.

9. The semiconductor nanocrystal composition of claim 6, wherein said one or more linking agents comprise an alkyl group.

10. The semiconductor nanocrystal composition of claim 1, wherein said core has a diameter from about 20 Å to about 100 Å.

11. The semiconductor nanocrystal composition of claim 1, wherein said core-overcoating shell is 1-10 monolayers thick.

12. The semiconductor nanocrystal composition of claim 1, wherein said core-overcoating shell epitaxially surrounds said core.

13. The semiconductor nanocrystal composition of claim 1, wherein said core/shell nanocrystal has an average cross-section that is no larger than about 20 nm.

14. The semiconductor nanocrystal composition of claim 1, wherein said core/shell nanocrystal has an average cross-section of about 1 nm to about 10 nm.

15. The semiconductor nanocrystal composition of claim 1, wherein said first semiconductor material comprises a Group II-VI semiconductor.

16. The semiconductor nanocrystal composition of claim 1, wherein said first semiconductor material comprises a Group III-V semiconductor.

17. The semiconductor nanocrystal composition of claim 1, wherein said first semiconductor material comprises MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, or HgTe.

18. The semiconductor nanocrystal composition of claim 1, wherein said first semiconductor material comprises GaAs, InGaAs, InP, or InAs.

19. The semiconductor nanocrystal composition of claim 1, wherein said second semiconductor material comprises a Group II-VI semiconductor.

20. The semiconductor nanocrystal composition of claim 1, wherein said second semiconductor material comprises a Group III-V semiconductor.

21. The semiconductor nanocrystal composition of claim 1, wherein said second semiconductor material comprises MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, or HgTe.

22. The semiconductor nanocrystal composition of claim 1, wherein said second semiconductor material comprises GaAs, InGaAs, InP, or InAs.

23. The semiconductor nanocrystal composition of claim 1, wherein said first semiconductor material comprises CdSe and the second semiconductor material comprises ZnS.

24. A semiconductor nanocrystal composition, comprising:
   a) a core comprising a first semiconductor material;
   b) a core-overcoating shell comprising a second semiconductor material, wherein the core and the core-overcoating shell form a core/shell nanocrystal; and,
   c) an encapsulating net surrounding the core/shell nanocrystal;
   wherein the core has an average cross-section no larger than 20 nanometers.

25. The semiconductor nanocrystal composition of claim 24, wherein said core has an average cross-section no larger than 10 nanometers.

26. The semiconductor nanocrystal composition of claim 24, wherein said nanocrystal core has an average cross-section in a range of from 1 nanometer to 10 nanometers.

27. The semiconductor nanocrystal composition of claim 24, wherein said encapsulating net comprises one or more linking agents capable of linking said core/shell nanocrystal to one or more affinity molecules.

28. The semiconductor nanocrystal composition of claim 27, wherein said one or more linking agents are polymerizable.

29. The semiconductor nanocrystal composition of claim 27, wherein said one or more linking agents comprise a thiol moiety.

30. The semiconductor nanocrystal composition of claim 27, wherein said one or more linking agents comprise an alkyl group.

31. The semiconductor nanocrystal composition of claim 24, wherein said first semiconductor material comprises a Group II-VI semiconductor.

32. The semiconductor nanocrystal composition of claim 24, wherein said first semiconductor material comprises a Group III-V semiconductor.

33. The semiconductor nanocrystal composition of claim 24, wherein said first semiconductor material comprises MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, or HgTe.

34. The semiconductor nanocrystal composition of claim 24, wherein said first semiconductor material comprises GaAs, InGaAs, InP, or InAs.

35. The semiconductor nanocrystal composition of claim 24, wherein said second semiconductor material comprises a Group II-VI semiconductor.

36. The semiconductor nanocrystal composition of claim 24, wherein said second semiconductor material comprises a Group III-V semiconductor.

37. The semiconductor nanocrystal composition of claim 24, wherein said second semiconductor material comprises MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, or HgTe.

38. The semiconductor nanocrystal composition of claim 24, wherein said second semiconductor material comprises GaAs, InGaAs, InP, or InAs.

39. The semiconductor nanocrystal composition of claim 24, wherein said first semiconductor material comprises CdSe and the second semiconductor material comprises ZnS.

* * * * *